United States Patent
Zhang et al.

(10) Patent No.: US 9,452,220 B2
(45) Date of Patent: Sep. 27, 2016

(54) COUPLING COMPOUNDS OF NSAID ANTI-INFLAMMATORY AND ANALGESIC DRUGS AND EGFR KINASE INHIBITORS, SYNTHESIS METHODS AND APPLICATIONS THEREOF

(71) Applicant: Guangzhou Institutes of Biomedicine and Health, Chinese Academy of Sciences, Guangdong (CN)

(72) Inventors: Yanmei Zhang, Guangdong (CN); Ke Ding, Guangdong (CN); Jinxi Liao, Guangdong (CN); Yican Wang, Guangdong (CN); Panyu Chen, Guangdong (CN)

(73) Assignee: GUANGZHOU INSTITUTES OF BIOMEDICINE AND HEALTH, CHINESE ACADEMY OF SCIENCES, Guangzhou (CN)

( * ) Notice: Subject to any disclaimer, the term of this patent is extended or adjusted under 35 U.S.C. 154(b) by 0 days.

(21) Appl. No.: 14/580,509

(22) Filed: Dec. 23, 2014

(65) Prior Publication Data
US 2016/0175453 A1    Jun. 23, 2016

(51) Int. Cl.
C07D 239/94    (2006.01)
C07D 403/12    (2006.01)
C07D 403/14    (2006.01)
C07D 405/12    (2006.01)
C07D 405/14    (2006.01)
A61K 47/48     (2006.01)

(52) U.S. Cl.
CPC ................ *A61K 47/48061* (2013.01)

(58) Field of Classification Search
CPC  C07D 239/94; C07D 403/12; C07D 403/14; C07D 405/12; C07D 405/14
See application file for complete search history.

*Primary Examiner* — Brian McDowell
(74) *Attorney, Agent, or Firm* — Wayne & King LLC

(57) ABSTRACT

The present invention discloses coupling compounds of a structure as shown in Formula I, II or III formed by connecting NSAID anti-inflammatory and analgesic drugs and EGFR inhibitors by ester bonds or pharmaceutically acceptable salts or stereoisomers thereof or prodrug molecules thereof:

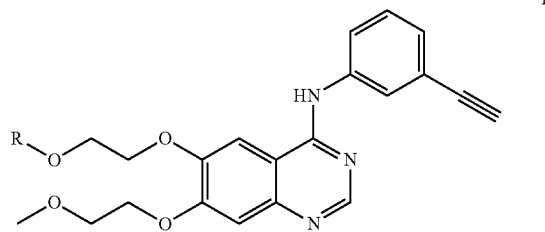

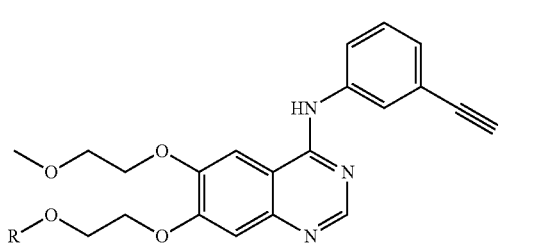

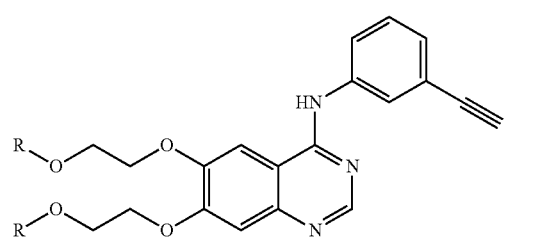

where R is a NSAID anti-inflammatory and analgesic drug. In the present invention, the coupling compounds obtained by coupling NSAID anti-inflammatory and analgesic drugs with EGFR inhibitors have excellent therapeutic effects of tumors and provide new drugs for clinic treatment options.

3 Claims, No Drawings

COUPLING COMPOUNDS OF NSAID ANTI-INFLAMMATORY AND ANALGESIC DRUGS AND EGFR KINASE INHIBITORS, SYNTHESIS METHODS AND APPLICATIONS THEREOF

TECHNICAL FIELD

The present invention belongs to the field of chemical pharmaceuticals, particularly relates to coupling compounds of NSAID anti-inflammatory and analgesic drugs and EGFR inhibitors or pharmaceutically acceptable salts or stereoisomers thereof and prodrug molecules thereof, synthesis methods thereof and applications thereof in synthesizing drugs.

BACKGROUND OF THE PRESENT INVENTION

Tumor is one of common diseases with high mortality in modern society. Conventional tumor treatment methods are mainly by surgical removal and preoperative and postoperative chemotherapy. However, the therapeutic effects of such methods are unsatisfactory. Targeted drugs have attracted much attention due to high specificity and low toxicity.

Studies in recent years indicate that the high expression of the epidermal growth factor (EGFR) is closely related to the occurrence, development and prognosis of tumors. Accordingly, targeted drugs specific for EGFR, including monoclonal antibodies (e.g., cetuximab, Matuzumab, etc.) and micromolecular tyrosine kinase inhibitors (e.g., gefitinib, erlotinib, lapatinib, etc.), have been successively developed and gradually applied in clinical practices for tumor treatment. Although EGFR inhibitors have achieved encouragingly therapeutic effects in clinical treatment of tumors because of their advantages of high selectivity and low toxicity, some of patients are insensitive to such treatment and some of patients eventually become resistant to such drugs.

In addition to EGFR, COX-2 is also regarded as a very promising target in tumor treatment. In recent years, it has been found from the studies both in China and at abroad that the expression of COX-2 obviously increases in many malignant tumor tissues. COX is a key enzyme in the synthesis process of prostaglandin. Cyclooxygenase-2 (COX-2), as an inducible enzyme, may be produced under the stimulation of many factors, playing an important role in the occurrence, development and spread of tumors. It mainly functions by suppressing the apoptosis, suppressing the anti-tumor function of the immune system, promoting the tumor angiogenesis, enhancing the invasiveness and other mechanisms.

Actually, there are many links between EGFR and the expression of COX-2. At present, some groups have proposed that the activation and over-expression of COX-2 is attributed to the activation of EGFR. EGFR is simulated by a ligand-amphiregulin (AR) thereof and thus induces the nucleus targeting of COX-2 in the polarized colonic epithelial cells, the release of PG and the subsequent mitosis. COX-2 inhibitors have showed that they can prevent a series of such behaviors.

Nonsteroidal anti-inflammatory drugs (NSAID), which are inhibitors of cyclooxygenase (COX), have been widely applied in clinic as anti-inflammatory, antipyretic and analgesic drugs. Some of such drugs, already as OTC drugs, may be directly obtained from drugstores without prescriptions. Clinical practices both in China and aboard over the years have indicated that NSAID anti-inflammatory and analgesic drugs can slow down the occurrence and development of a wide range of tumors. The studies of tumor treatment by NSAID anti-inflammatory and analgesic drugs mostly focus on colon cancer. It has been found from animal models, in-vitro pharmacological experiments, therapeutic tests or epidemiological surveys that NSAIDs can prevent the occurrence of colon cancer in the early stage.

SUMMARY OF THE PRESENT INVENTION

One of objectives of the present invention is to provide coupling compounds of NSAID anti-inflammatory and analgesic drugs and EGFR inhibitors or pharmaceutically acceptable salts or stereoisomers thereof and prodrug molecules thereof, with excellent therapeutic effects of tumors (particularly lung cancer).

This objective is realized by the following technical solution:

Coupling compounds of a structure as shown in Formula I, II or III formed by connecting NSAID anti-inflammatory and analgesic drugs and EGFR inhibitors by ester bonds or pharmaceutically acceptable salts or stereoisomers thereof or prodrug molecules thereof are provided:

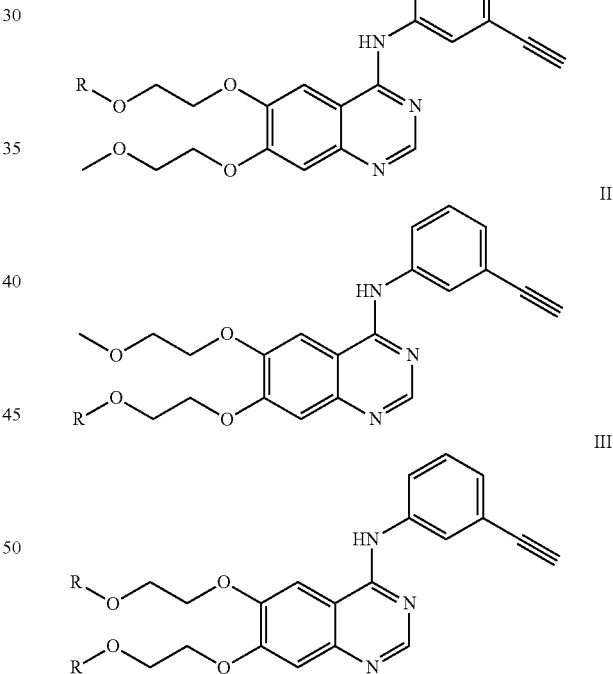

where R is an NSAID anti-inflammatory and analgesic drug. Preferably, the NSAID anti-inflammatory and analgesic drug may have different chemical structures, including but not limited to: ketoprofen (2-(4-benzoylphenyl)propanoic acid, $C_{16}H_{14}O_3$), ibuprofen (2-(4-isobutylbenzene)propanoic acid, $C_{13}H_{18}O_2$), SC-75416 (7-tert-butyl-6-chloro-2-(trifluoromethyl)-2H-benzopyran-3-carboxylic acid, $C_{15}H_{14}ClF_3O_3$), aspirin ((acetoxy)benzoic acid, $C_9H_8O_4$), naproxen ((+)-α-methyl-6-methoxy-2-naphthylacetic acid, $C_{14}H_{14}O_3$), indometacin (2-methyl-1-(4-chlorobenzoyl)-5-methoxy-1H-indol-3-carboxylic acid, $C_{19}H_{16}ClNO_4$), sulindac ((Z)-5-fluoro-2-methyl-1-[(4-methylsulfinylpenyl)methylene)-1H-indene-3-carboxyl ic acid, $C_{20}H_{17}FO_3S$), and tamibarotene (4-(5,5,8,8-tetramethyl-5,6,7,8-tetralin-2-alkenylcarbamyl)benzoic acid, $C_{22}H_{25}NO_3$).

Another objective of the present invention is to provide a synthesis method of the coupling compounds.

This objective is realized by the following technical solution:

A synthesis method of coupling compounds formed by connecting NSAID anti-inflammatory and analgesic drugs and EGFR inhibitors by ester bonds is provided. The synthesis method comprises the following steps of:

1) under appropriate conditions, esterifying an NSAID anti-inflammatory and analgesic drug with haloalkane or alcohol to obtain an intermediate of esterification, where the appropriate conditions comprise conditions for esterification of acyl chloride or activated carboxylic ester with alcohol, conditions for direct acid-alcohol condensation, or conditions for esterification of carboxylic acid or salts thereof with halides; and etherifying the resulting intermediate of esterification with phenolic hydroxyl groups or salts thereof contained in an EGFR inhibitor of a structure as shown in Formula IV, V or VI to obtain coupling compounds;

IV

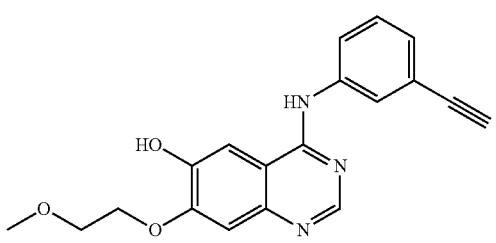

V

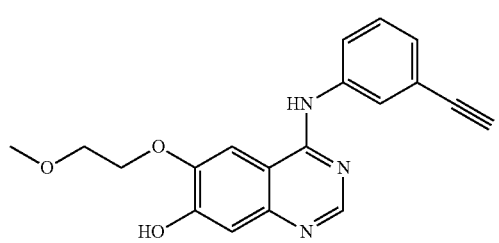

VI

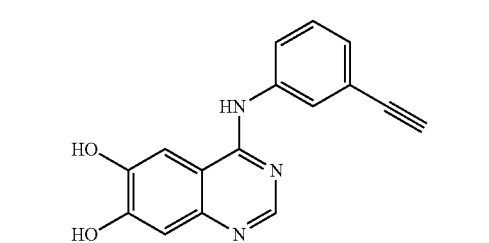

or 2) esterifying the NSAID anti-inflammatory and analgesic drug with phenolic hydroxyl groups contained in an EGFR inhibitor of a structure as shown in Formula VII, VIII or IX or salts thereof to obtain coupling compounds;

VII

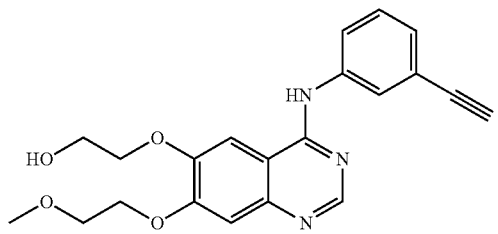

VIII

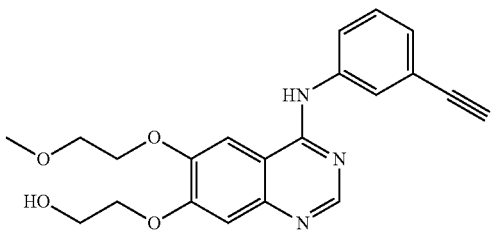

IX

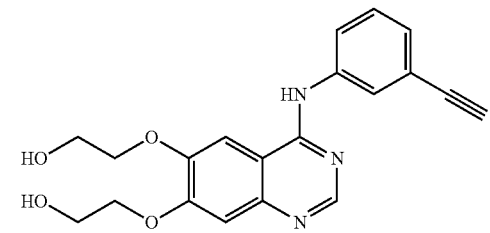

The NSAID anti-inflammatory and analgesic drug comprises any one of the NSAID anti-inflammatory and analgesic drugs, and acids, carboxylates, acyl chlorides and activated carboxylic esters thereof.

The alcohol is 2-bromoethanol, 2-chloroethanol or 2-iodoethanol; and, the haloalkane is 1,2-dibromoethane, 1-bromo-2-chloroethane or 1,2-dichloroethane.

Another objective of the present invention is to provide pharmaceutical compositions for treating tumors.

This objective is realized by the following technical solution:

Pharmaceutical compositions for treating tumors are provided, the pharmaceutically active ingredients of which include the coupling compounds formed by connecting NSAID anti-inflammatory and analgesic drugs and EGFR inhibitors by ester bonds or pharmaceutically acceptable salts or stereoisomers thereof or prodrug molecules thereof.

Another objective of the present invention is to provide applications of the coupling compounds formed by connecting NSAID anti-inflammatory and analgesic drugs and EGFR inhibitors by ester bonds or pharmaceutically acceptable salts or stereoisomers thereof or prodrug molecules thereof.

The tumor includes non-small cell lung cancer, small cell lung cancer, lung adenocarcinoma, lung squamous carcinoma, pancreatic cancer, breast cancer, prostate cancer, liver cancer, skin cancer, epithelial cell carcinoma, gastrointestinal stromal tumor, leukemia, histiocytic lymphoma, nasopharyngeal carcinoma, colorectal cancer, etc.

This objective is realized by the following technical solution:

Applications of the coupling compounds formed by connecting NSAID anti-inflammatory and analgesic drugs and EGFR inhibitors by ester bonds or pharmaceutically acceptable salts or stereoisomers thereof or prodrug molecules thereof in preparing drugs for tumors are provided.

In the present invention, new chemical entities are obtained by coupling NSAID anti-inflammatory and analgesic drugs with EGFR inhibitors, and the coupling compounds obtained by coupling NSAID anti-inflammatory and analgesic drugs with EGFR inhibitors have excellent therapeutic effects of tumors (particularly lung cancer) and provide new drugs for clinic treatment options.

DETAILED DESCRIPTION OF THE PRESENT INVENTION

Specific implementations of the present invention will be described as below by embodiments. However, these embodiments are not intended to limit the protection scope of the present invention.

Embodiment 1

Synthesis of 2-(4-(3-ethynylaniline)-7-(2-methoxyethoxy)quinazoline-6-oxy)ethyl-2-(4-benzoylbenzene)propanoic acid

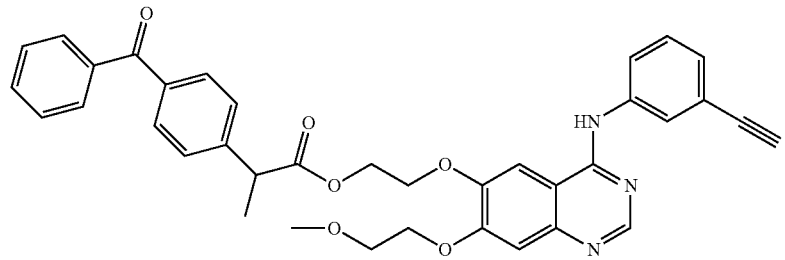 [SMILES: C#Cc1cccc(Nc2ncnc3cc(OCCOC)c(OCCOC(=O)C(C)c4ccc(C(=O)c5ccccc5)cc4)cc23)c1]

Step 1

Synthesis of ethyl 3-hydroxy-4-(2-methoxyethoxy) benzoate

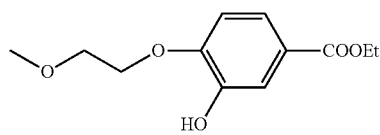

10.9 g of ethyl 3,4-dihydroxybenzoate was dissolved in 40 ml of dry DMF (dimethylformamide); then, 3.6 g NaH was slowly added into the mixture in an ice bath; 10 min later, under argon, a solution of 8.34 g of 1-bromo-2-methoxyethane and 100 mg of Kl in 10 ml of dry DMF was added dropwise into the mixture within 3 hrs; and the reaction temperature was kept at 0° C. during this process. At the end of dropping, the reaction temperature was allowed to naturally rise up to room temperature. The reaction was kept overnight and followed by TLC until finished. The reaction solution was diluted with water, extracted with ethyl acetate, washed with saturated sodium chloride solution and dried with anhydrous sodium sulfate. The crude product was separated by column chromatography to obtain 7.2 g of the resulting product ethyl 3-hydroxy-4-(2-methoxyethoxy) benzoate (50%).

$^1$H NMR (400 MHz, CDCl$_3$) δ 7.59 (dd, J=8.4, 1.6 Hz, 1H), 7.53 (d, J=1.2 Hz, 1H), 6.87 (d, J=8.4 Hz, H), 4.28 (q, J=7.2 Hz, 2H), 4.13 (t, J=4.4 Hz, 2H), 3.66 (t, J=4.4 Hz, 2H), 3.35 (s, 3H), 1.31 (t, J=7.2 Hz, 3H)

Step 2

Synthesis of ethyl 3-(2-acetoxylethoxy)-4-(2-methoxyethoxy) benzoate

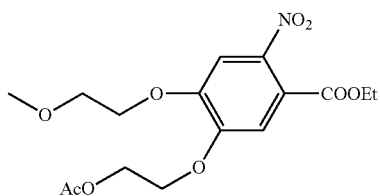 [SMILES: CCOC(=O)c1cc(OCCOC(C)=O)c(OCCOC)cc1[N+](=O)[O-]]

7.2 g of the resulting product ethyl 3-hydroxy-4-(2-methoxyethoxy) benzoate obtained in step 1 was dissolved in 10 ml of dry DMF, then 4.6 g of 2-2-bromoethyl acetate and 1.2 g of anhydrous K$_2$CO$_3$ were added into the mixture, and the system was reacted overnight at 60° C. The reaction was followed by TLC until finished. The reaction solution was diluted with water, extracted with ethyl acetate, washed with saturated sodium chloride solution, dried with anhydrous sodium sulfate and concentrated in vacuum to obtain 7.5 g of the resulting product ethyl 3-(2-acetoxylethoxy)-4-(2-methoxyethoxy) benzoate (77%).

$^1$H NMR (400 MHz, CDCl$_3$) δ 7.59 (d, J=8.4 Hz, 1 H), 7.52 (s, 1 H), 6.85 (d, J=8.4 Hz, 1H), 4.39 (t, J=4.4 Hz, 2 H), 4.29 (q, J=6.8 Hz, 2 H), 4.20 (t, J=4.4 Hz, 2 H), 4.13 (t, J=4.4 Hz, 2 H), 3.72 (t, J=4.4 Hz, 2 H), 3.79 (s, 3 H), 2.01 (s, 3 H), 1.32 (t, J=6.8 Hz, 3 H)

Step 3 Synthesis of ethyl 5-(2-acetoxylethoxy)-4-(2-methoxyethoxy)-2-nitrobenzoate 8 g of the resulting product ethyl 3-(2-acetoxylethoxy)-4-(2-methoxyethoxy) benzoate obtained in step 2 was dissolved in 24 ml of glacial acetic acid; then, 2.4 ml of concentrated nitric acid was added dropwise into the mixture in an ice-salt bath, the system was stirred for 1 hr at 0° C. and added dropwise with 2.4 ml of concentrated sulfuric acid; and the system was allowed to naturally rise up to room temperature and reacted overnight. The reaction solution was diluted with water, extracted with DCM (dichloromethane), washed with saturated sodium chloride solution, dried with anhydrous sodium sulfate and concentrated in vacuum to obtain 6.8 g of the resulting product ethyl 5-(2-acetoxylethoxy)-4-(2-methoxyethoxy)-2-nitrobenzoate (75%).

$^1$H NMR (400 MHz, CDCl3) δ 7.46(s, 1 H), 7.09 (s, 1 H), 4.44 (t, J=4.4 Hz, 2 H), 4.35 (q, J=6.8 Hz, 2 H), 4.28 (t, J=4.4 Hz, 2 H), 4.22 (t, J=4.4 Hz, 2 H), 3.77 (t, J=4.4 Hz, 2 H), 3.41 (s, 3 H), 2.06 (s, 3 H), 1.32 (t, J=6.8 Hz, 3 H)

ESI$^+$ m/z 372.0 (M+H)$^+$

Step 4 Synthesis of ethyl 5-(2-acetoxylethoxy)-4-(2-methoxyethoxy)-2-aminobenzoate

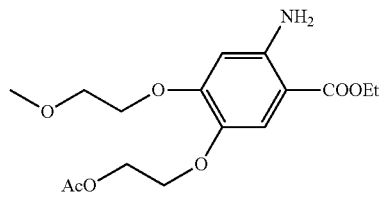 [SMILES: CCOC(=O)c1cc(OCCOC(C)=O)c(OCCOC)cc1N]

6.8 g of the resulting product ethyl 5-(2-acetoxylethoxy)-4-(2-methoxyethoxy)-2-nitrobenzoate obtained in step 3 was dissolved in 81 ml of ethanol, and then 27.1 ml of water and 2.7 ml of concentrated hydrochloric acid were added into the mixture. The system was heated and vigorously stirred in an oil bath, then slowly added with 10.3 g of iron powder in batches, heated, refluxed for 0.5 hrs and followed by TLC until the reaction finished. The reaction solution was filtered, and the filter cake was washed with DCM. The filtrate was diluted with water, extracted with DCM, washed with saturated sodium chloride solution, dried with anhydrous sodium sulfate and concentrated in vacuum to obtain 6.2 g of the resulting product ethyl 5-(2-acetoxylethoxy)-4-(2-methoxyethoxy)-2-aminobenzoate (100%).

ESI$^+$ m/z 342.0 (M+H)$^+$

Step 5 Synthesis of ethyl 2-(7-(2-methoxyethoxy)-4-oxa-3,4-dihydroxyquinazoline-6-oxy) acetate

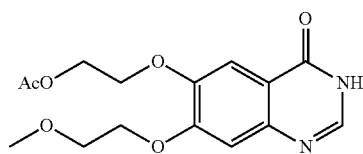 [SMILES: COCCOc1cc2nc[nH]c(=O)c2cc1OCCOC(C)=O]

6 g of the resulting product ethyl 5-(2-acetoxylethoxy)-4-(2-methoxyethoxy)-2-aminobenzoate obtained in step 4 was dissolved in 28 ml of formamide, and then 1 g of ammonium formate was added into the mixture. The system was heated to 180° C., reacted for 3 hrs and followed by TLC until the reaction finished. The reaction solution was diluted with water, extracted with DCM, washed with saturated sodium chloride solution, dried with anhydrous sodium sulfate and concentrated in vacuum to obtain 4 g of the resulting product ethyl 2-(7-(2-methoxyethoxy)-4-oxa-3,4-dihydroxyquinazoline-6-oxy) acetate (70%).

ESI$^+$ m/z 323.0 (M+H)$^+$

Step 6 Synthesis of ethyl 2-(4-(3-ethynylaniline)-7-(2-methoxyethoxy)quinazoline-6-oxy) acetate

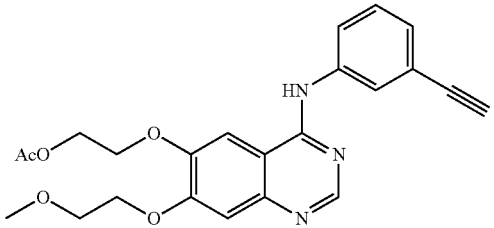 [SMILES: C#Cc1cccc(Nc2ncnc3cc(OCCOC)c(OCCOC(C)=O)cc23)c1]

In an ice bath, 3 g of the resulting product ethyl 2-(7-(2-methoxyethoxy)-4-oxa-3,4-dihydroxyquinazoline-6-oxy) acetate obtained in step 5 was added dropwise into 20 ml of POCl$_3$, and the system was heated to 110° C., refluxed for 1 hr and followed by TLC until the reaction finished The reaction solution was concentrated in vacuum and diluted with water, extracted with ethyl acetate, washed with saturated sodium chloride solution, dried with anhydrous sodium sulfate and concentrated in vacuum to obtain 3 g of intermediate ethyl 2-(4-chloro-7-(2-methoxyethoxy)quinazoline-6-oxy) acetate. The intermediate was suspended in 30 ml of isopropanol, and the mixture was added with 1 ml of 3-aminophenylacetylene, refluxed overnight at 80° C. and followed by TLC until the reaction finished. The reaction solution was concentrated in vacuum to obtain 3.1 g of the resulting product ethyl 2-(4-(3-ethynylaniline)-7-(2-methoxyethoxy) quinazoline-6-oxy) acetate (79%).

ESI$^+$ m/z 422.1 (M+H)$^+$

Step 7 Synthesis of 2-(4-(3-ethynylaniline)-7-(2-methoxyethoxy)quinazoline-6-oxy) ethanol

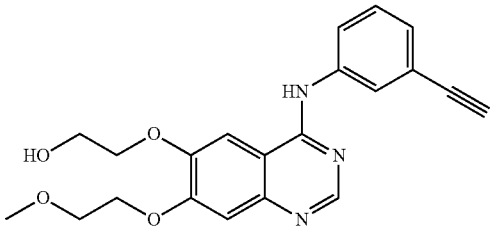 [SMILES: C#Cc1cccc(Nc2ncnc3cc(OCCOC)c(OCCO)cc23)c1]

3.1 g of the resulting product ethyl 2-(4-(3-ethynylaniline)-7-(2-methoxyethoxy) quinazoline-6-oxy) acetate obtained in step 6 was dissolved in 20 ml of methanol, and then the mixture was added with 1 g of KOH, stirred overnight and followed by TLC until the reaction finished. The reaction solution was concentrated in vacuum to obtain 2.3 g of the resulting product 2-(4-(3-ethynylaniline)-7-(2-methoxyethoxy)quinazoline-6-oxy)ethanol (82%).

$^1$H NMR (400 MHz, MeOD) δ 8.43 (s, 1 H), 7.93 (s, 1 H), 7.79-7.74 (m, 2 H), 7.40 (t, J=8.0 Hz, 1 H), 7.28 (d, J=7.6 Hz, 1 H), 7.17 (s, 1 H), 4.36 (t, J=4.4 Hz, 2 H), 4.25 (t, J=4.4 Hz, 2 H), 4.00 (t, J=4.4 Hz, 2 H), 3.90 (t, J=4.4 Hz, 2 H), 3.53 (s, 1 H), 3.50 (s, 3 H)

ESI$^+$ m/z 380.0 (M+H)$^+$

Step 8 Synthesis of 2-(4-(3-ethynylaniline)-7-(2-methoxyethoxy) quinazoline-6-oxy)ethyl-2-(4-benzoylbenzene)propanoic acid

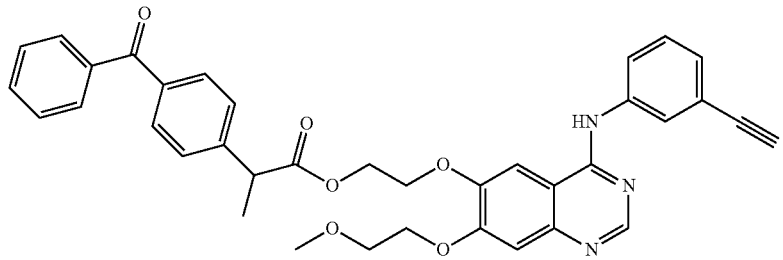 [SMILES: C#Cc1cccc(Nc2ncnc3cc(OCCOC)c(OCCOC(=O)C(C)c4ccc(C(=O)c5ccccc5)cc4)cc23)c1]

400 mg of ketoprofen was dissolved in 2 ml of dry DCM, and then the mixture was added with 0.16 mg of oxalyl chloride in an ice bath and added with 1 drop of DMF. The system was heated from 0° C. to room temperature and reacted for 2 hrs and then concentrated in vacuum to obtain acyl chloride for standby.

130 mg of the resulting product 2-(4-(3-ethynylaniline)-7-(2-methoxyethoxy) quinazoline-6-oxy)ethanol obtained in step 7 was dissolved in 6 ml of dry THF, and then the mixture was added with 0.23 ml of dry $Et_3N$ in an ice bath, stirred for 10 min and added with a solution of the acyl chloride in 2 ml of dry THF. The system was allowed to naturally rise up to room temperature, reacted overnight and followed by TLC until the reaction finished. The reaction solution was diluted with water, extracted with ethyl acetate, washed with saturated sodium chloride solution, dried with anhydrous sodium sulfate and concentrated in vacuum. The crude product was separated by column chromatography to obtain 210 mg of resulting product 2-(4-(3-ethynylaniline)-7-(2-methoxyethoxy)quinazoline-6-oxy)ethyl-2-(4-benzoylbenzene)propanoic acid (95%).

$^1$H NMR (400 MHz, $CDCl_3$) δ 8.64 (s, 1 H), 8.28 (br., 1 H), 7.98 (s, 1 H), 7.91 (d, J=8.0 Hz, 1 H), 7.62 (s, 1 H), 7.30-7.03 (m, 7 H), 4.45-4.35 (m, 2 H), 4.20-4.18 (m, 4 H), 3.79-3.74 (m, 3 H), 3.40 (s, 3 H), 3.08 (s, 1 H), 2.40 (d, J=6.8 Hz, 2 H), 1.82-1.75 (m, 1 H), 1.53 (d, J=7.2 Hz, 3 H), 0.86 (d, J=6.4 Hz, 6 H); $^{13}$C NMR (125 MHz, $CDCl_3$) δ 196.6, 173.6, 156.3, 153.7, 153.2, 148.3, 146.7, 140.5, 138.9, 137.5, 137.0, 132.4, 131.5, 129.8, 128.85, 128.78, 128.6, 128.3, 128.1, 127.3, 125.1, 122.4, 106.3, 108.2, 102.9, 83.3, 77.34, 77.26, 77.0, 76.7, 70.6, 68.6, 62.4, 58.9, 45.0, 18.3

$ESI^+$ m/z 616.3 $(M+H)^+$

Embodiment 2

Synthesis of 2-(4-(3-ethynylaniline)-7-(2-methoxyethoxy)quinazoline-6-oxy)ethyl-2-(4-isobutylbenzene)propanoic acid

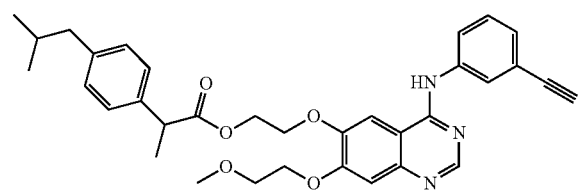 [SMILES: C#Cc1cccc(Nc2ncnc3cc(OCCOC)c(OCCOC(=O)C(C)c4ccc(CC(C)C)cc4)cc23)c1]

The synthesis method is similar to Embodiment 1.

$^1$H NMR (400 MHz, $CDCl_3$) δ 8.59 (s, 1 H), 7.83 (s, 1 H), 7.73 (d, J=8.0 Hz, 1 H), 7.31-7.00 (m, 8 H), 4.52-4.46 (m, 1 H), 4.42-4.36 (m, 1 H), 4.16-4.14 (m, 4 H), 3.73-3.68 (m, 3 H), 3.40 (s, 3 H), 3.06 (s, 1 H), 2.39 (d, J=7.2 Hz, 2 H), 1.81 (m, 1 H), 1.47 (d, J=7.2 Hz, 3 H), 0.85 (d, J=6.4 Hz, 6 H); $^{13}$C NMR (125 MHz, $CDCl_3$) δ 174.5, 156.4, 154.1, 153.4, 148.6, 147.1, 140.5, 138.8, 137.3, 129.4, 129.2, 128.8, 127.6, 127.0, 125.1, 122.6, 122.4, 109.3, 108.5, 103.4, 83.3, 77.4, 77.3, 76.7, 70.8, 69.2, 66.5, 62.3, 59.2, 44.9, 29.6, 22.3, 18.5, 13.9

$ESI^+$ m/z 568.3 $(M+H)^+$

Embodiment 3

Synthesis of 2-(4-(3-ethynylaniline)-7-(2-methoxyethoxy)quinazoline-6-oxy)ethyl-2-acetoxybenzoic acid

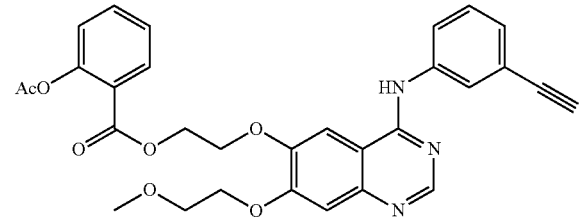 [SMILES: C#Cc1cccc(Nc2ncnc3cc(OCCOC)c(OCCOC(=O)c4ccccc4OC(C)=O)cc23)c1]

The synthesis method is similar to Embodiment 1, where acyl chloride used in step 8 is purchased not self-manufactured.

$^1$H NMR (400 MHz, $CDCl_3$) δ 8.61 (s, 1 H), 8.08 (br., 1 H), 7.96 (d, J=8.0 Hz, 1 H), 7.83-7.80 (m, 1 H), 7.72 (d, J=8.0 Hz, 1 H), 7.51 (dt, J=1.6, 8.0 Hz, 1 H), 7.29-7.16 (m, 5 H), 7.06 (d, J=8.0 Hz, 1 H), 4.62 (t, J=4.0 Hz, 2 H), 4.31 (t, J=4.0 Hz, 2 H), 4.12 (t, J=4.0 Hz, 2 H), 3.70 (t, J=4.4 Hz, 2 H), 3.34 (s, 3 H), 3.09 (s, 1 H), 2.31 (s, 3 H); $^{13}$C NMR (125 MHz, $CDCl_3$) δ 169.8, 164.0, 156.3, 153.9, 153.4, 150.6, 148.6, 133.9, 131.7, 129.9, 128.8, 127.5, 125.9, 123.6, 122.5, 122.3, 119.1, 117.4, 109.4, 108.6, 103.0, 83.3, 77.4, 77.3, 77.0, 76.7, 70.6, 68.9, 66.5, 62.8, 20.8

$ESI^+$ m/z 542.0 $(M+H)^+$

Embodiment 4

Synthesis of 2-(4-(3-ethynylaniline)-7-(2-methoxyethoxy)quinazoline-6-oxy)ethyl-2-(6-methoxylnaphthyl-2-ene)propanoic acid

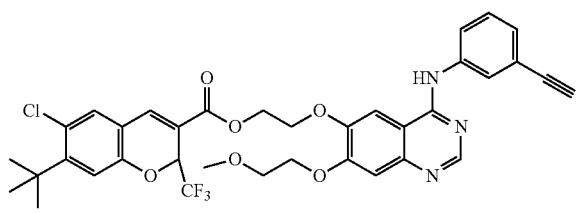 [SMILES: C#Cc1cccc(Nc2ncnc3cc(OCCOC)c(OCCOC(=O)C4=Cc5cc(Cl)c(C(C)(C)C)cc5OC4C(F)(F)F)cc23)c1]

The synthesis method is similar to Embodiment 1.

$^1$H NMR (400 MHz, CDCl$_3$) δ 8.62 (s, 1 H), 7.89-7.05 (m, 9 H), 5.71-5.70 (m, 1 H), 4.68 (m, 2 H), 4.37-4.28 (m, 4 H), 3.82 (m, 2 H), 3.45 (s, 3 H), 3.11 (s, 1 H), 1.47 (s, 9 H); $^{13}$C NMR (125 MHz, CDCl$_3$) δ 163.4, 156.3, 154.2, 152.4, 151.6, 148.8, 138.7, 136.3, 131.8, 129.0, 127.9, 126.9, 125.1, 122.8, 122.4, 117.5, 116.2, 115.5, 109.2, 103.0, 87.3, 77.5, 77.3, 77.0, 76.7, 70.9, 69.3, 66.5, 63.2, 59.2, 29.7, 29.6, 29.3, 29.2

Embodiment 5

Synthesis of 2-(4-(3-ethynylaniline)-7-(2-methoxyethoxy)quinazoline-6-oxy)ethyl-7-tert-butyl-6-chloro-2-(trifluoromethyl)-2H-pyran-3-carboxylic acid

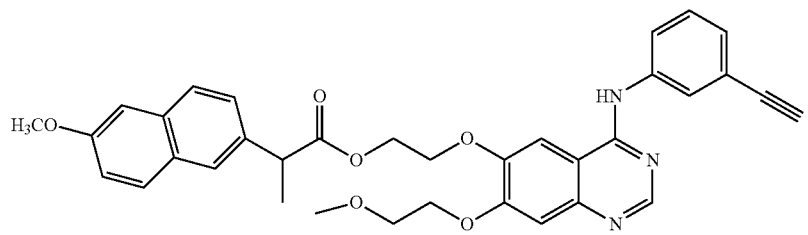 [SMILES: C#Cc1cccc(Nc2ncnc3cc(OCCOC)c(OCCOC(=O)C(C)c4ccc5cc(OC)ccc5c4)cc23)c1]

The synthesis method is similar to Embodiment 1.

$^1$H NMR (400 MHz, CDCl$_3$) δ 8.66 (s, 1 H), 7.89 (s, 1 H), 7.79 (d, J=8.0 Hz, 1 H), 7.62-7.59 (m, 3 H), 7.39-7.02 (m, 8 H), 4.54-4.52 (m, 2 H), 4.27 (t, J=4.4 Hz, 2 H), 4.10 (t, J=4.4 Hz, 2 H), 3.91-3.87 (m, 4 H), 3.68 (t, J=4.4 Hz, 2 H), 3.42 (s, 3 H), 3.12 (s, 1 H), 1.59 (d, J=6.8 Hz, 3 H); $^{13}$C NMR (125 MHz, CDCl$_3$) δ 174.4, 157.6, 157.4, 156.3, 154.0, 153.4, 148.3, 147.1, 138.8, 135.2, 133.6, 133.5, 132.1, 130.8, 129.1, 128.8, 128.7, 127.5, 127.3, 127.1, 126.9, 126.0, 125.8, 125.7, 125.1, 124.6, 122.5, 122.3, 121.8, 118.9, 118.7, 109.2, 108.3, 105.4, 103.2, 83.3, 77.4, 77.3, 77.0, 76.7, 70.6, 69.0, 66.4, 62.3, 59.0, 55.1, 45.1, 18.4 ESI$^+$ m/z 592.3 (M+H)$^+$

Embodiment 6

Synthesis of 3-(4-(3-ethynylaniline)-7-(2-methoxyethoxy)quinazoline-6-oxy)ethyl-2-(1-(4-chlorobenzoyl)-5-methoxy-2-methyl-1H-indol-3-ene)acetic acid

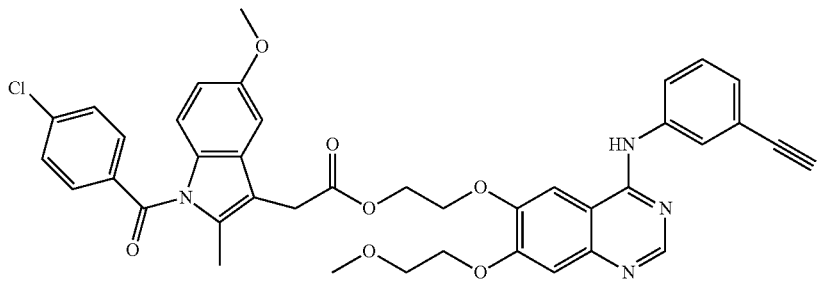 [SMILES: C#Cc1cccc(Nc2ncnc3cc(OCCOC)c(OCCOC(=O)Cc4c(C)n(C(=O)c5ccc(Cl)cc5)c5ccc(OC)cc45)cc23)c1]

The synthesis method is similar to Embodiment 1.

$^1$H NMR (400 MHz, CDCl$_3$) δ 8.64 (s, 1 H), 7.86 (s, 1 H), 7.76 (t, J=8.4 Hz, 1 H), 7.61 (d, J=8.4 Hz, 2 H), 7.42 (d, J=8.4 Hz, 2 H), 7.36 (t, J=8.0 Hz, 1 H), 7.27 (d, J=5.2 Hz, 1 H), 7.21 (dd, J=2.4, 10.0 Hz, 2 H), 6.94 (s, 1 H), 6.84 (d,

J=8.8 Hz, 1 H), 6.63 (dd, J=2.4, 8.8 Hz, 1 H), 4.54(m, 2 H), 4.50 (m, 2 H), 4.17 (m, 2 H), 3.75-3.68 (m, 6 H), 3.42 (s, 3 H), 3.09 (s, 1 H), 2.33 (s, 1 H), 1.56 (d, J=7.2 Hz, 3 H); $^{13}$C NMR (125 MHz, CDCl$_3$) δ171.8, 170.6, 168.3, 156.3, 156.0, 154.3, 154.1, 154.0, 153.6, 148.7, 147.3, 139.2, 138.8, 136.0, 133.8, 131.1, 130.7, 130.5, 129.0, 128.9, 127.7, 125.0, 122.8, 122.3, 114.9, 112.2, 111.5, 110.9, 110.7, 109.4, 108.9, 102.9, 101.3, 83.3, 77.3, 77.0, 76.7, 70.9, 69.2, 66.7, 62.7, 59.2, 55.6, 30.8, 13.3

ESI$^+$ m/z 719.2 M$^+$

Embodiment 7

Synthesis of (E)-2-(4-(3-ethynylaniline)-7-(2-methoxyethoxy)quinazoline 6-oxy)ethyl-2-(5-fluoro-2-methyl-1-(4-methylsulfinyl)benzylidene)-1H-indene-3-ene)acetic acid

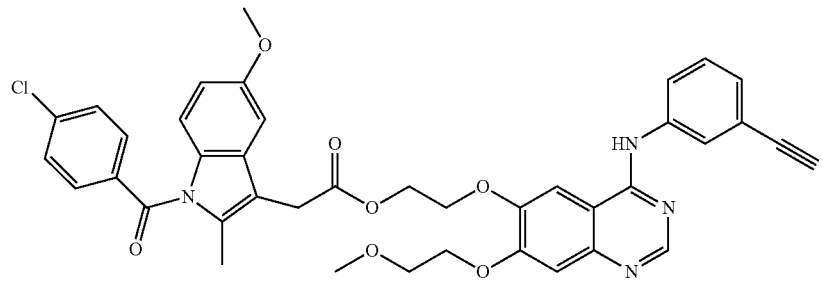 [SMILES: C#Cc1cccc(Nc2ncnc3cc(OCCOC)c(OCCOC(=O)Cc4c(C)n(C(=O)c5ccc(Cl)cc5)c5ccc(OC)cc45)cc23)c1]

Steps 1, 2, 3, 4, 5, 6 and 7 are similar to those in Embodiment 1.

Step 8

Synthesis of (E)-2-(4-(3-ethynylaniline)-7-(2-methoxyethoxy)quinazoline 6-oxy)ethyl-2-(5-fluoro-2-methyl-1-(4-methylsulfinyl)benzylidene)-1H-indene-3-ene)acetic acid 159 mg of sulindac was dissolved in 2 ml of dry THF, and then the mixture was added with 184 mg of DCC (N,N'-dicyclohexylcarbodiimide). The system was allowed to naturally rise up to room temperature and reacted for 1 hr to synthesize active ester. 100 mg of the resulting product 2-(4-(3-ethynylaniline)-7-(2-methoxyethoxy)quinazoline-6-oxy)ethanol obtained in step 7 of Embodiment 1 was dissolved in 6 ml of dry THF (tetrahydrofuran), and then the mixture was added with 11 mg of DMAP (4-dimethylaminopyridine) and added with the active ester in an ice bath under argon. The system was allowed to naturally rise up to room temperature, reacted overnight, and followed by TLC until the reaction finished. The reaction solution was filtered and washed with DCM. The filtrate was concentrated in vacuum and separated by column chromatography to obtain 189 mg of the resulting product (E)-2-(4-(3-ethynylaniline)-7-(2-methoxyethoxy)quinazoline-6-oxy)ethyl-2-(5-fluoro-2-methyl-1-(4-methylsulfinyl)benzylidene)-1H-indene-3-ene)acetic acid (88%).

$^1$H NMR (400 MHz, CDCl$_3$) δ 8.73 (s, 1 H), 7.87 (s, 1 H), 7.78-7.07 (m, 12 H), 6.86-6.83 (m, 1 H), 6.51-6.47 (m, 1 H), 4.56 (t, J=4.4 Hz, 2 H), 4.31 (t, J=4.8 Hz, 2 H), 4.23 (t, J=4.4 Hz, 2 H), 3.77 (t, J=4.8 Hz, 2 H), 3.60-3.56 (m, 2 H), 3.43 (s, 3 H), 3.08 (s, 1 H), 2.79 (s, 3 H), 2.18 (s, 3 H); $^{13}$C NMR (125 MHz, CDCl$_3$) δ

ESI$^+$ m/z 718.4 (M+H)$^+$

Embodiment 8

Synthesis of 2-(4-(3-ethynylaniline)-7-(2-methoxyethoxy)quinazoline-6-oxy)ethyl-4-(5,5,8,8-tetramethyl-5,6,7,8-tetralin-2-alkenylcarbamyl)benzoic acid

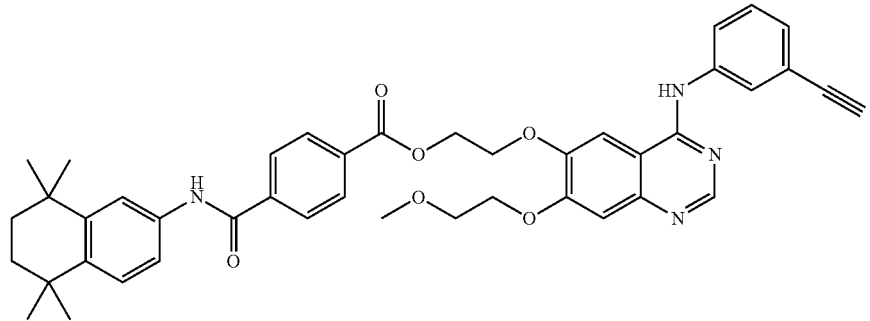 [SMILES: C#Cc1cccc(Nc2ncnc3cc(OCCOC)c(OCCOC(=O)c4ccc(C(=O)Nc5ccc6c(c5)C(C)(C)CCC6(C)C)cc4)cc23)c1]

The synthesis method is similar to Embodiment 6.

$^1$H NMR (400 MHz, CDCl$_3$) δ 8.81 (s, 1 H), 8.54 (s, 1 H), 7.95 (d, J=8.4 Hz, 2 H), 7.82 (d, J=8.8 Hz, 3 H), 7.72 (d, J=8.0 Hz, 1 H), 7.57 (s, 1 H), 7.48-7.44 (m, 2 H), 7.23-7.15 (m, 4 H), 4.63 (s, 2 H), 4.31 (s, 2 H), 3.59 (s, 2 H), 3.24(s, 3 H), 3.04 (s, 1 H), 1.63 (s, 4 H), 1.24-1.24 (m, 12 H); $^{13}$C NMR (125 MHz, CDCl$_3$) δ165.4, 165.3, 156.5, 153.9, 153.5, 148.6, 147.0, 145.7, 141.7, 139.2, 138.8, 135.1, 132.0, 129.7, 128.8, 127.6, 127.1, 127.0, 125.2, 122.54, 122.49, 118.4, 118.3, 109.5, 108.7, 103.1, 83.3, 77.5, 77.3, 77.0, 76.7, 70.6, 68.9, 66.6, 63.0, 59.0, 34.9, 34.3, 33.9, 31.7
ESI⁺ m/z 713.5 (M+H)⁺

Embodiment 9

Synthesis of 2-(4-(3-ethynylaniline)-6-(2-methoxyethoxy)quinazoline-7-oxy)ethyl-2-(benzoylphenyl)propanoic acid

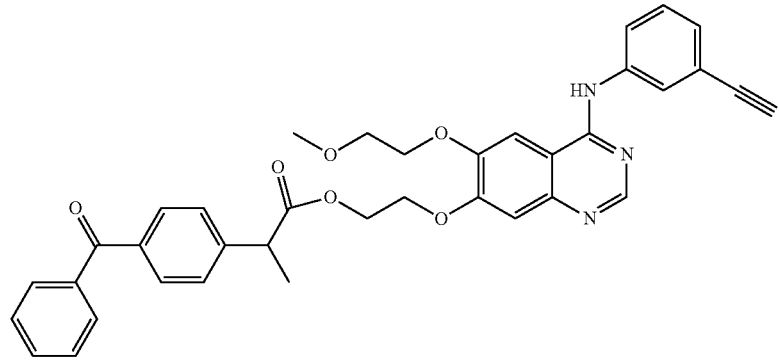 [SMILES: C#Cc1cccc(Nc2ncnc3cc(OCCOC(=O)C(C)c4ccc(C(=O)c5ccccc5)cc4)c(OCCOC)cc23)c1]

Step 1

Synthesis of 6,7-dimethoxyquinazolinone

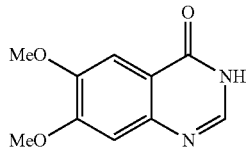

30 g of methyl 2-amino-4,5-dimethoxybenzoate was suspended in 240 ml of formamide, and the system was heated to 140° C. and reacted for 24 hrs. A large amount of solids was precipitated in the flask. The reaction solution was filtered after cooled. The filter cake was washed with a small amount of water and then dried to obtain 29.3 g of the resulting product (87%).

¹H NMR (400 MHz, DMSO) δ 12.01(br., 1 H), 7.99 (s, 1 H), 7.44 (s, 1 H), 7.13 (s, 1 H), 3.90 (s, 3 H), 3.87 (s, 3 H)

Step 2

Synthesis of 6,7-dihydroxyquinazolinone

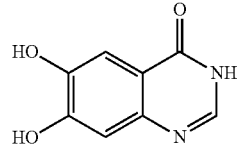

10 g of the resulting product synthesized in step 1 was added in 85 ml of 40% HBr solution, and then the mixture was slowly added with 30 ml of acetic anhydride in a water bath. The water bath is removed, and the system was heated to 110° C. in an oil bath, reacted for 1 hr, then heated to 140° C. and reacted for 30 hrs. A large amount of white solids was precipitated in the flask. The reaction solution was filtered after cooled. The filter cake was dissolved in 75 ml of water, and the mixture was added with aqua ammonia until the pH value was adjusted to 9 and then filtered. The filter cake was washed with 75 ml of 1M NaHCO₃ solution and dried to obtain 6.5 g of the resulting product (75%). ¹H NMR (400 MHz, DMSO) δ 7.78 (s, 1 H), 7.29 (s, 1 H), 6.84 (s, 1 H)

Step 3

Synthesis of 6,7-diacetoxylquinazolinone

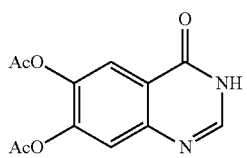 [SMILES: CC(=O)Oc1cc2nc[nH]c(=O)c2cc1OC(C)=O]

7.6 g of the resulting product 6,7-dihydroxyquinazolinone synthesized in step 2 was added with 40 ml of acetic anhydride and 1 ml of pyridine, and then the system was heated to 130° C., refluxed and reacted for 6 hrs and cooled to room temperature. The reaction solution was poured into 100 ml of water and stirred, and a large amount of grey solids was precipitated. The mixture was filtered. The filter cake was washed with a small amount of water and dried to obtain 9 g of the resulting product 6,7-diacetoxylquinazolinone (80%).

¹H NMR (400 MHz, DMSO) δ 12.41(s, 1 H), 8.13 (s, 1 H), 7.97 (s, 1 H), 7.60 (s, 1 H), 2.34 (s, 3 H), 2.32(s, 3 H)

Step 4

Synthesis of 6,7-diacetoxyl-4-anilinoquinazoline

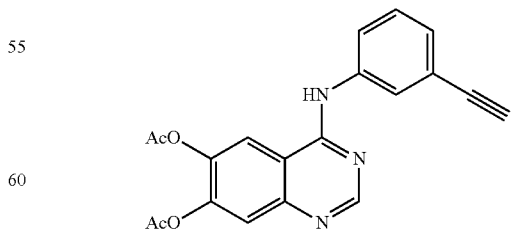

4 g of the resulting product 6,7-diacetoxylquinazolinone synthesized in step 3 was suspended in 100 ml of chloroform, and then the mixture was added dropwise with 10 ml of phosphorus oxychloride in an ice bath. At the end of dropping phosphorus oxychloride, the ice bath was removed. The system was heated to 70° C. and reacted for 2 hrs. The reaction solution was cooled to room temperature and added with 15 ml of triethylamine in an ice bath. The system continued to be heated to 70° C. and reacted for 12 hrs. After concentrated in vacuum, the reaction solution was diluted with water, extracted with ethyl acetate, washed with saturated sodium chloride solution, dried with anhydrous sodium sulfate and concentrated in vacuum to obtain 3.4 g of intermediate chlorinated product 6,7-diacetoxyl-4-chloroquinazoline. The chlorinated product was added with 60 ml of isopropanol and 1.34 g of 3-ethynylaniline. The system was heated to 70° C. and reacted overnight, and a large amount of solids was precipitated in the system. The reaction solution is filtered after cooled. The filter cake was washed with a small amount of isopropanol to obtain 3 g of the resulting product 6,7-diacetoxyl-4-anilinoquinazoline (55%).

$^1$H NMR (400 MHz, DMSO) δ 11.53 (br., 1 H), 8.96-8.93 (m, 2 H), 7.94-7.93 (m, 2 H), 7.80 (d, J=8.4 Hz, 1 H), 7.53 (t, J=8.0 Hz, 1 H), 7.43 (d, J=8.0 Hz, 1 H), 4.30 (s, 1 H), 2.43 (s, 3 H), 2.40 (s, 3 H)

Step 5

Synthesis of 6,7-dihydroxy-4-anilinoquinazoline

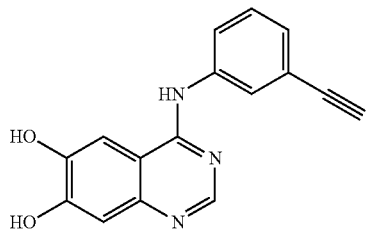 [SMILES: C#Cc1cccc(Nc2ncnc3cc(O)c(O)cc23)c1]

3 g of the resulting product 6,7-diacetoxyl-4-anilinoquinazoline obtained in step 4 was dissolved in 40 ml of methanol, and then the mixture was added with 5 ml of aqua ammonia. The system was reacted at room temperature, and followed by TLC until the reaction finished. The reaction solution was concentrated in vacuum to obtain 2.3 g of the resulting product 6,7-dihydroxy-4-anilinoquinazoline (100%).

$^1$H NMR (400 MHz, DMSO) δ 9.87 (br., 1 H), 8.52 (s, 1 H), 8.00 (s, 1 H), 7.85 (s, 1 H), 7.41-7.19 (m, 4 H), 4.27 (s, 1 H)

ESI$^+$ m/z 278.0 (M+H)$^+$

Step 6

Synthesis of 4-(3-ethynylaniline)-6-(2-methoxyethoxy)quinazoline-7-olcohol

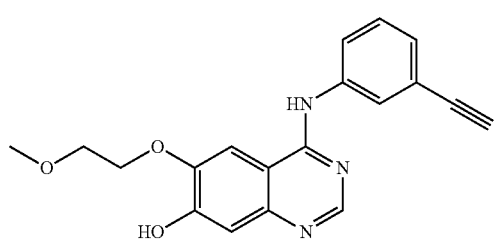 [SMILES: C#Cc1cccc(Nc2ncnc3cc(O)c(OCCOC)cc23)c1]

1 g of the resulting product 6,7-dihydroxy-4-anilinoquinazoline obtained in step 5 was dissolved with 10 ml of dry DMF, and then mixture was added with 1 g of anhydrous potassium carbonate and 486 mg of 2-bromoethylmethyl ether. The system was maintained at 20° C. and reacted for 2d. The reaction solution was diluted with water, extracted with ethyl acetate, washed with saturated sodium chloride solution, dried with anhydrous sodium sulfate and concentrated in vacuum. The crude product was separated by column chromatography to obtain 620 mg of the resulting product 4-(3-ethynylaniline)-6-(2-methoxyethoxy)quinazoline-7-olcohol (62%).

$^1$H NMR (400 MHz, MeOD) δ 8.42 (s, 1 H), 7.93 (s, 1 H), 7.79-7.75 (m, 1 H), 7.71 (s, 1 H), 7.40 (t, J=8.0 Hz, 1 H), 7.29-7.26 (m, 1 H), 7.21 (m, 1 H), 4.39 (t, J=4.4 Hz, 2 H), 3.93 (t, J=4.4 Hz, 2 H), 3.51 (s, 4 H)

Step 7

Synthesis of 4-(4-benzoylpenyl)-1-bromo-3-pentanone

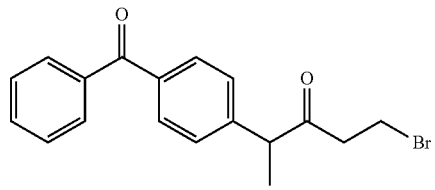 [SMILES: CC(C(=O)CCBr)c1ccc(C(=O)c2ccccc2)cc1]

2 g of ketoprofen was added in 3 ml of 2-bromoethanol, and the mixture was added dropwise with 1.2 ml of thionyl chloride in an ice bath. The reaction solution was heated to 80° C. and reacted, and the system was followed by TLC until the reaction finished. The reaction solution was diluted with water, extracted with ethyl acetate, washed with saturated sodium chloride solution, dried with anhydrous sodium sulfate and concentrated in vacuum. The crude product was separated by column chromatography to obtain 1.9 g of the resulting product 4-(4-benzoylpenyl)-1-bromo-3-pentanone (70%).

$^1$H NMR (400 MHz, CDCl$_3$) δ 7.81-7.76 (m, 3 H), 7.69 (d, J=8.0 Hz, 1 H), 7.61-7.55 (m, 2 H), 7.50-7.43 (m, 3 H), 4.40 (dt, J=2.4, 6.0, 8.4 Hz, 2 H), 3.87 (q, J=7.2 Hz, 1 H), 3.47 (t, J=6.0 Hz, 2 H), 1.57 (d, J=7.2 Hz, 3 H)

ESI$^+$ m/z 362.2 (M+H)$^+$

Step 8

Synthesis of 2-(4-(3-ethynylaniline)-6-(2-methoxyethoxy)quinazoline-7-oxy)ethyl-2-(benzoylphenyl)propanoic acid

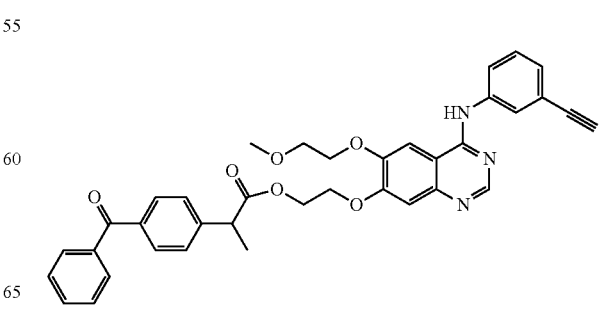

100 mg of the resulting product 4-(3-ethynylaniline)-6-(2-methoxyethoxy) quinazoline-7-olcohol obtained in step 6 was added with 150 mg of the resulting product 4-(4-benzoylpenyl)-1-bromo-3-pentanone obtained in step 7, 124 mg of anhydrous potassium carbonate, 25 mg of potassium iodide and 3 ml of dry DMF. The system was reacted at 40° C., and followed by TLC until the reaction finished. The reaction solution was diluted with water, extracted with ethyl acetate, washed with saturated sodium chloride solution, dried with anhydrous sodium sulfate and concentrated in vacuum. The crude product was separated by column chromatography to obtain 152 mg of the resulting product 2-(4-(3-ethynylaniline)-6-(2-methoxyethoxy)quinazoline-7-oxy)ethyl-2-(benzoylphenyl)propanoic acid (83%).

$^1$H NMR (400 MHz, CDCl$_3$) δ 8.13 (s, 1 H), 7.93-7.20 (m, 14 H), 4.53-4.44 (m, 2 H), 4.28-4.18 (m, 4 H), 3.91 (q, J=7.2 Hz, 1 H), 3.82 (t, J=4.8 Hz, 2 H), 3.43(s, 3 H), 3.04 (s, 1 H), 1.60 (d, J=7.2 Hz, 3 H); $^{13}$C NMR (125 MHz, CDCl$_3$) δ 196.9, 174.7, 156.4, 154.3, 153.8, 147.9, 147.7, 140.6, 139.1, 137.9, 137.2, 132.6, 131.5, 129.9, 129.3, 128.9, 128.8, 128.6, 128.2, 127.4, 124.8, 122.6, 122.0, 109.3, 109.0, 103.5, 83.5, 77.3, 77.0, 76.7, 70.4, 68.3, 66.6, 61.9, 59.2, 45.4, 18.3

ESI$^+$ m/z 616.3 (M+H)$^+$

Embodiment 10

Synthesis of 2-(4-(3-ethynylaniline)-6-(2-methoxyethoxy)quinazoline-7-oxy)ethyl-2-(4-isobutylphenyl) propanoic acid

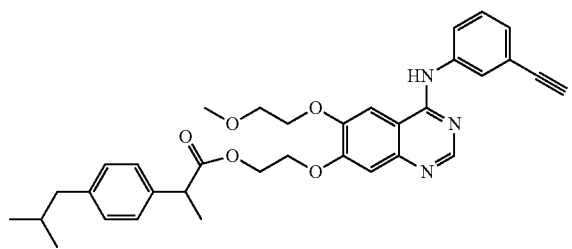 [SMILES: C#Cc1cccc(Nc2ncnc3cc(OCCOC(=O)C(C)c4ccc(CC(C)C)cc4)c(OCCOC)cc23)c1]

Steps 1, 2, 3, 4, 5 and 6 are similar to those in Embodiment 9.

Step 7

Synthesis of 2-bromoethyl-2-(4-isobutylphenyl)propanoic acid

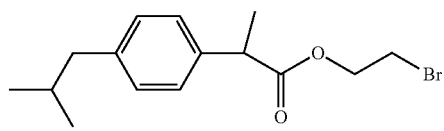 [SMILES: CC(C)Cc1ccc(C(C)C(=O)OCCBr)cc1]

The synthesis method is similar to step 7 in Embodiment 9.

$^1$H NMR (400 MHz, CDCl$_3$) δ 7.24 (d, J=8.0 Hz, 2 H), 7.12 (d, J=8.0 Hz, 2 H), 4.42-4.30(m, 2 H), 3.78 (q, J=7.2 Hz, 1 H), 3.47 (dt, J=0.8, 6.0, 6.4 Hz, 2 H), 2.47 (d, J=7.2 Hz, 2 H), 1.91-1.80 (m, 1 H), 1.53 (d, J=7.2 Hz, 3 H), 0.92 (d, J=6.8 Hz, 6 H)

ESI$^+$ m/z 313.8 (M+H)$^+$

Step 8

Synthesis of 2-(4-(3-ethynylaniline)-6-(2-methoxyethoxy)quinazoline-7-oxy)ethyl-2-(4-isobutylphenyl) propanoic acid

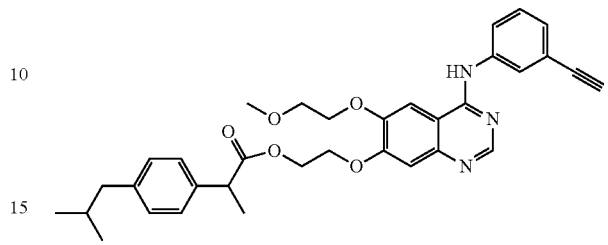

$^1$H NMR (400 MHz, CDCl$_3$) δ 8.64 (s, 1 H), 8.28 (br., 1 H), 7.98 (s, 1 H), 7.91 (d, J=8.0 Hz, 1 H), 7.62 (s, 1 H), 7.30-7.03 (m, 7 H), 4.45-4.35 (m, 2 H), 4.20-4.18 (m, 4 H), 3.79-3.74 (m, 3 H), 3.40 (s, 3 H), 3.08 (s, 1 H), 2.40 (d, J=6.8 Hz, 2 H), 1.82-1.75 (m, 1 H), 1.53 (d, J=7.2 Hz, 3 H), 0.86 (d, J=6.4 Hz, 6 H); $^{13}$C NMR (125 MHz, CDCl$_3$) δ 175.3, 156.3, 153.9, 153.4, 147.8, 146.9, 140.5, 139.1, 137.0, 129.2, 128.6, 127.1, 126.9, 124.5, 122.4, 121.7, 109.1, 108.2, 102.5, 83.3, 77.26, 77.23, 77.0, 76.7, 70.2, 68.1, 66.0, 61.4, 58.9, 44.8, 44.7, 29.9, 29.5, 22.1, 18.3

Embodiment 11

Synthesis of 2-(4-(3-ethynylaniline)-6-(2-methoxyethoxy)quinazoline-7-oxy)ethyl-2-acetoxyl benzoic acid

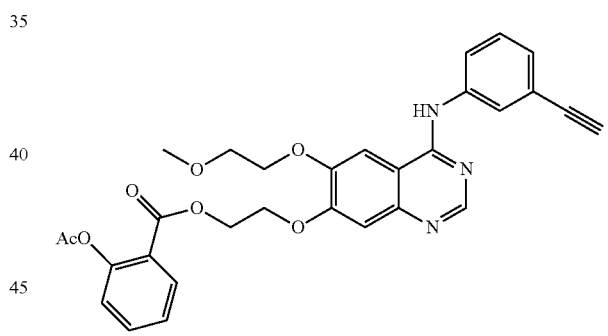

Steps 1, 2, 3, 4, 5 and 6 are similar to those in Embodiment 9.

Step 7

Synthesis of 4-(3-ethynylaniline)-6-(2-methoxyethoxy)quinazoline-7-olcohol

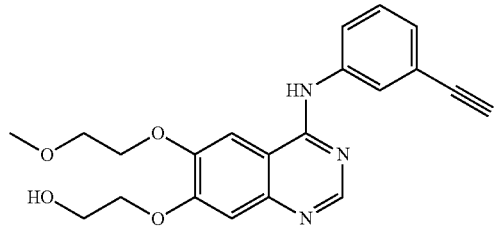 [SMILES: C#Cc1cccc(Nc2ncnc3cc(OCCO)c(OCCOC)cc23)c1]

400 mg of the resulting product 4-(3-ethynylaniline)-6-(2-methoxyethoxy) quinazoline-7-olcohol obtained in step 6 of Embodiment 9 was added with 240 mg of 2-bromoethyl acetate, 307 mg of anhydrous potassium carbonate, 20 mg of potassium iodide and 4 ml of dry DMF. The system was reacted at 40° C., and followed by TLC until the reaction finished. The reaction solution was diluted with water, extracted with ethyl acetate, washed with saturated sodium chloride solution, dried with anhydrous sodium sulfate and concentrated in vacuum. The crude product was directly put into the next step of reaction without separation.

The crude product was dissolved in 5 ml of methanol and then added with 200 mg of KOH. The system was reacted overnight at room temperature and followed by TLC until the reaction finished. The reaction solution was directly concentrated in vacuum and separated by column chromatography to obtain 389 mg of the resulting product (86%).

Step 8

Synthesis of 2-(4-(3-ethynylaniline)-6-(2-methoxyethoxy)quinazoline-7-oxy)ethyl-2-acetoxyl benzoic acid

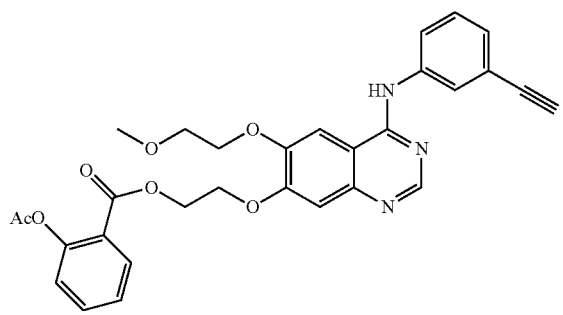 [SMILES: C#Cc1cccc(Nc2ncnc3cc(OCCOC(=O)c4ccccc4OC(C)=O)c(OCCOC)cc23)c1]

300 mg of the resulting product 4-(3-ethynylaniline)-6-(2-methoxyethoxy) quinazoline-7-olcohol obtained in step 7 was dissolved in 10 ml of dry THF, and then the mixture was added with 0.25 ml of dry Et$_3$N in an ice bath, stirred for 10 min and then added with 344 mg of o-acetylbenzoyl chloride. The system was allowed to naturally rise up to room temperature, reacted overnight and followed by TLC until the reaction finished. The reaction solution was diluted with water, extracted with ethyl acetate, washed with saturated sodium chloride solution, dried with anhydrous sodium sulfate and concentrated in vacuum. The crude product was separated by column chromatography to obtain 240 mg of the resulting product 2-(4-(3-ethynylaniline)-6-(2-methoxyethoxy)quinazoline-7-oxy)ethyl-2-acetoxyl benzoic acid (56%).

$^1$H NMR (400 MHz, CDCl3) δ 8.55 (s, 1H), 8.51 (br., 1H), 7.79-6.68 (m, 10H), 4.49 (m, 2H), 4.15-4.08 (m, 4H), 3.67 (m, 2H), 3.30 (s, 3H), 3.08 (s, 1H), 2.26 (s, 3H); $^{13}$C NMR (125 MHz, CDCl3) δ 170.2, 164.0, 156.3, 154.0, 153.2, 150.1, 147.8, 138.8, 135.6, 133.8, 131.3, 129.6, 128.4, 127.1, 125.7, 124.9, 124.8, 123.3, 122.3, 122.1, 118.9, 117.1, 109.0, 107.9, 83.23, 83.19, 77.3, 77.0, 76.7, 70.0, 68.0, 62.8, 58.7, 20.7

Embodiment 12

Synthesis of 2-(4-(3-ethynylaniline)-6-(2-methoxyethoxy)quinazoline-7-oxy)ethyl-7-tert-butyl-6-chloro-2-(trifluoromethyl)-2H-pyran-3-carboxylic acid

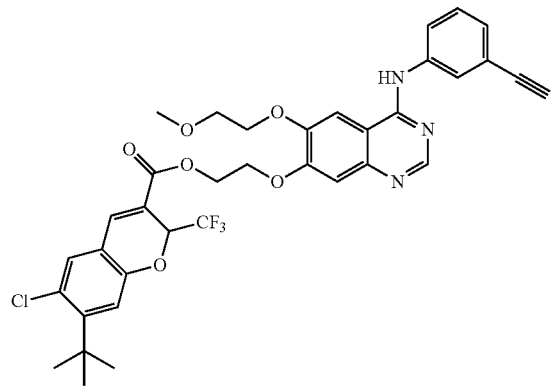 [SMILES: C#Cc1cccc(Nc2ncnc3cc(OCCOC(=O)C4=Cc5cc(Cl)c(C(C)(C)C)cc5OC4C(F)(F)F)c(OCCOC)cc23)c1]

Steps 1, 2, 3, 4, 5 and 6 are similar to those in Embodiment 9.

Step 7

Synthesis of 2-bromoethyl-7-tert-butyl-6-chloro-2-(trifluoromethyl)-2H-benzopyran-3-carboxylic acid

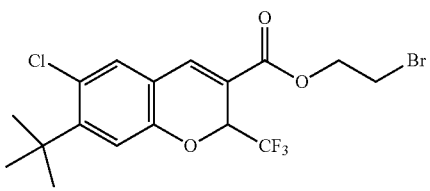 [SMILES: CC(C)(C)c1cc2c(cc1Cl)C=C(C(=O)OCCBr)C(C(F)(F)F)O2]

The synthesis method is similar to step 7 in Embodiment 9.

$^1$H NMR (400 MHz, CDCl$_3$) δ 7.69(s, 1H), 7.22 (s, 1H), 7.06 (s, 1H), 5.74 (q, J=6.8 Hz, 1H), 4.63-4.53 (m, 2H), 3.63 (t, J=6.4 Hz, 2H), 1.48 (s, 9H)

Step 8

Synthesis of 2-(4-(3-ethynylaniline)-6-(2-methoxyethoxy)quinazoline-7-oxy)ethyl-7-tert-butyl-6-chloro-2-(trifluoromethyl)-2H-pyran-3-carboxylic acid The synthesis method is similar to step 8 in Embodiment 9.

$^1$H NMR (400 MHz, CDCl$_3$) δ 8.67(s, 1H), 7.92-7.02 (m, 10H), 5.72-5.70 (m, 1H), 4.70-4.65 (m, 2H), 4.42-4.39 (m, 2H), 4.28-4.26 (m, 2H), 4.14-4.11 (m, 2H), 3.45 (s, 3H), 3.11 (s, 1H), 1.46 (s, 9H)

Embodiment 13

Synthesis of 2-(4-(3-ethynylaniline)-6-(2-methoxy-ethoxy)quinazoline-7-oxy)ethyl-2-(6-methoxylnaphthyl-2-ene)propanoic acid

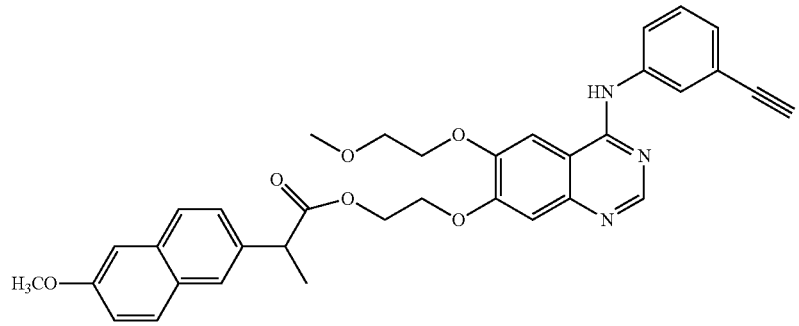 [SMILES: C#Cc1cccc(Nc2ncnc3cc(OCCOC(=O)C(C)c4ccc5cc(OC)ccc5c4)c(OCCOC)cc23)c1]

Steps 1, 2, 3, 4, 5 and 6 are similar to those in Embodiment 9.

Step 7

Synthesis of 2-bromoethyl-2-(6-methoxylnaphthyl-2-ene)propanoic acid

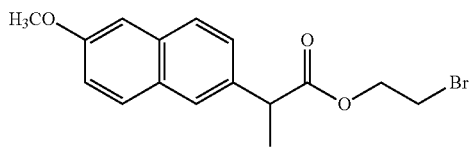 [SMILES: COc1ccc2cc(C(C)C(=O)OCCBr)ccc2c1]

The synthesis method is similar to step 7 in Embodiment 9.

$^1$H NMR (400 MHz, CDCl$_3$) δ 7.72-7.69(m, 3H), 7.43 (dd, J=1.6, 8.4 Hz, 1 H), 7.16-7.12 (m, 2H), 4.44-4.32 (m, 2H), 3.95-3.86 (m, 4H), 3.47 (dt, J=1.2, 6.0, 7.2 Hz, 2H), 1.62 (d, J=7.2 Hz, 3H)

Step 8

Synthesis of 2-(4-(3-ethynylaniline)-6-(2-methoxy-ethoxy)quinazoline-7-oxy)ethyl-2-(6-methoxylnaphthyl-2-ene)propanoic acid

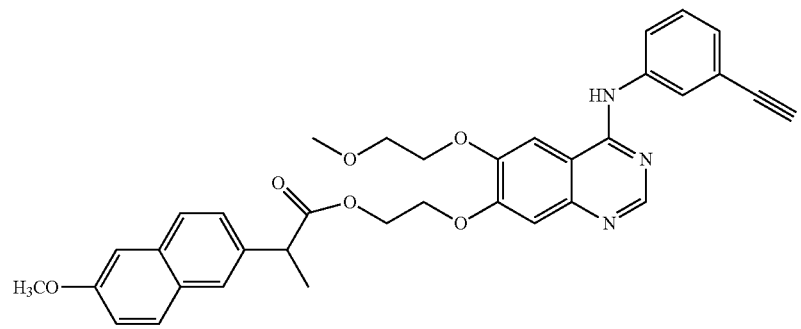 [SMILES: C#Cc1cccc(Nc2ncnc3cc(OCCOC(=O)C(C)c4ccc5cc(OC)ccc5c4)c(OCCOC)cc23)c1]

The synthesis method is similar to step 8 in Embodiment 9.

$^1$H NMR (400 MHz, CDCl$_3$) δ 8.12 (s, 1H), 8.01-7.04 (m, 13H), 4.44 (m, 2H), 4.19 (m, 4H), 3.88 (m, 4H), 3.76 (m, 2H), 3.40 (s, 3H), 3.10 (s, 1H), 1.63 (d, J=7.2 Hz, 3H); $^{13}$C NMR (125 MHz, CDCl$_3$) δ 175.3, 157.5, 156.2, 153.9, 153.5, 147.8, 147.1, 139.1, 134.9, 133.5, 129.0, 128.7, 127.2, 127.1, 124.5, 122.5, 121.7, 118.9, 109.1, 108.5, 105.4, 102.5, 83.4, 77.29, 77.25, 77.0, 76.7, 70.2, 68.1, 66.0, 65.5, 61.5, 59.0, 45.2, 18.3

ESI$^+$ m/z 591.7 M$^+$

Embodiment 14

Synthesis of 3-(4-(3-ethynylaniline)-6-(2-methoxyethoxy)quinazoline-7-oxy)ethyl-2-(1-(4-chlorobenzoyl)-5-methoxy-2-methyl-1H-indol-3-ene)acetic acid

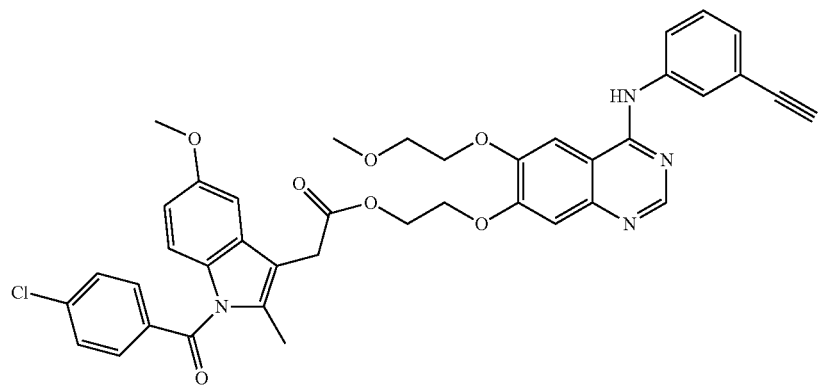 [SMILES: C#Cc1cccc(Nc2ncnc3cc(OCCOC(=O)Cc4c(C)n(C(=O)c5ccc(Cl)cc5)c5ccc(OC)cc45)c(OCCOC)cc23)c1]

Steps 1, 2, 3, 4, 5 and 6 are similar to those in Embodiment 9.

Step 7

Synthesis of 2-bromoethyl-2-(1-(4-chlorobenzoyl)-5-methoxy-2-methyl-1H-indol-3-ene)acetic acid

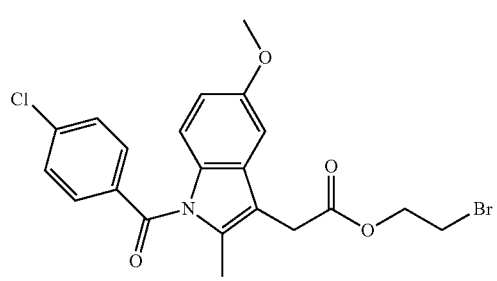 [SMILES: COc1ccc2c(c1)c(CC(=O)OCCBr)c(C)n2C(=O)c1ccc(Cl)cc1]

The synthesis method is similar to step 7 in Embodiment 9.

$^1$H NMR (400 MHz, CDCl$_3$) δ 7.67 (d, J=8.4 Hz, 2H), 7.48 (d, J=8.4 Hz, 2H), 6.98 (d, J=2.4 Hz, 1H), 6.89 (d, J=9.2 Hz, 1H), 6.69 (dd, J=2.8, 9.2 Hz, 1H), 4.43 (t, J=6.0 Hz, 2H), 3.84 (s, 3H), 3.71 (s, 2H), 3.52 (t, J=6.0 Hz, 2H), 2.40 (s, 3H) ESI$^+$ m/z 464.2 M$^+$

Step 8

Synthesis of 3-(4-(3-ethynylaniline)-6-(2-methoxyethoxy)quinazoline-7-oxy)ethyl-2-(1-(4-chlorobenzoyl)-5-methoxy-2-methyl-1H-indol-3-ene)acetic acid The synthesis method is similar to step 8 in Embodiment 9.

$^1$H NMR (400 MHz, CDCl$_3$) δ 8.59 (s, 1H), 8.20 (s, 1H), 7.89 (s, 1H), 7.63-7.12 (m, 9H), 6.90 (s, 1H), 6.77 (d, J=8.8 Hz, 1H), 6.58 (d, J=8.8 Hz, 1H), 4.39 (m, 2H), 3.78-3.66 (m, 7H), 3.37 (s, 3H), 3.05 (s, 1H), 2.30 (s, 3H); $^{13}$C NMR (125 MHz, CDCl$_3$) δ 171.1, 168.1, 156.3, 155.7, 154.1, 153.5, 147.8, 147.2, 139.1, 138.8, 135.9, 133.4, 130.9, 130.6, 130.3, 128.9, 128.6, 127.3, 124.8, 122.4, 122.0, 114.7, 112.0, 111.1, 109.1, 108.4, 103.2, 101.4, 83.3, 77.3, 77.0, 76.7, 70.2, 68.0, 66.7, 62.2, 58.9, 55.4, 29.9, 13.1

Embodiment 15

Synthesis of (E)-2-(4-(3-ethynylaniline)-6-(2-methoxyethoxy)quinazoline-7-oxy)ethyl-2-(5-fluoro-2-methyl-1-(4-methylsulfinyl)benzylidene)-1H-indene-3-ene)acetic acid

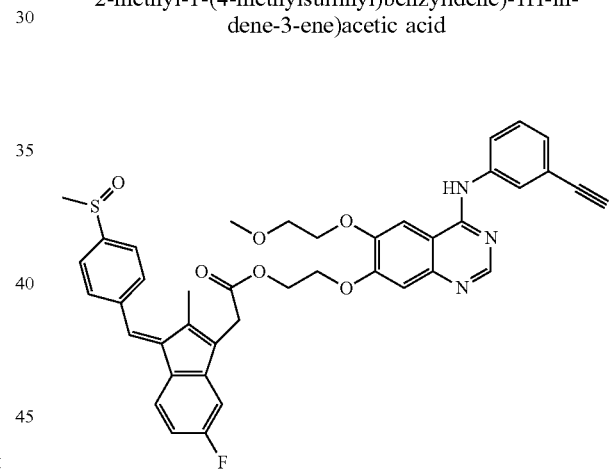

Steps 1, 2, 3, 4, 5, 6 and 7 are similar to those in Embodiment 9.

Step 8

Synthesis of (E)-2-(4-(3-ethynylaniline)-6-(2-methoxyethoxy)quinazoline-7-oxy)ethyl-2-(5-fluoro-2-methyl-1-(4-methylsulfinyl)benzylidene)-1H-indene-3-ene)acetic acid The synthesis method is similar to step 8 in Embodiment 7.

$^1$H NMR (400 MHz, CDCl$_3$) δ 8.66 (s, 1H), 7.98 (s, 1H), 7.71-7.10 (m, 11H), 6.87 (dd, J=2.0, 8.8 Hz, 1H), 6.58-6.47 (m, 1H), 4.55 (t, J=5.6 Hz, 2H), 4.34 (t, J=5.6 Hz, 2H), 4.26 (t, J=4.4 Hz, 2H), 3.83 (t, J=4.4 Hz, 2H), 3.63 (s, 2H), 3.44 (s, 3H), 3.07 (s, 1H), 2.79 (s, 3H), 2.16 (s, 3H)

ESI$^+$ m/z 718.1 (M+H)$^+$

Embodiment 16

Synthesis of 2-(4-(3-ethynylaniline)-6-(2-methoxy-ethoxy)quinazoline-7-oxy)ethyl-4-(5,5,8,8-tetramethyl-5,6,7,8-tetralin-2-alkenylcarbamyl)benzoic acid

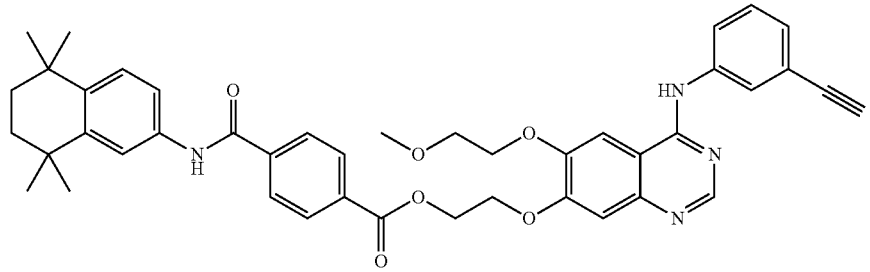 [SMILES: C#Cc1cccc(Nc2ncnc3cc(OCCOC(=O)c4ccc(C(=O)Nc5ccc6c(c5)C(C)(C)CCC6(C)C)cc4)c(OCCOC)cc23)c1]

Steps 1, 2, 3, 4, 5 and 6 are similar to those in Embodiment 9.

Step 7

Synthesis of 2-bromoethyl-4-(5,5,8,8-tetramethyl-5,6,7,8-tetralin-2-alkenylcarbamyl)benzoic acid

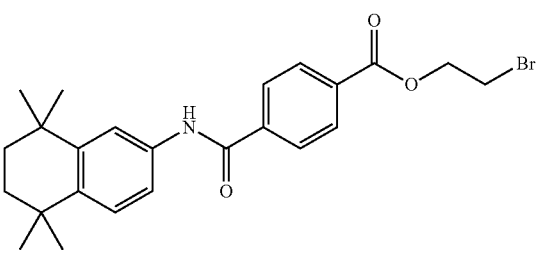 [SMILES: CC1(C)CCC(C)(C)c2cc(NC(=O)c3ccc(C(=O)OCCBr)cc3)ccc21]

The synthesis method is similar to step 7 in Embodiment 9.

$^1$H NMR (400 MHz, CDCl$_3$) δ 8.16 (d, J=8.0 Hz, 2H), 7.94 (d, J=8.4 Hz, 2H), 7.54 (s, 1H), 7.45 (d, J=8.0 Hz, 1H), 7.32 (d, J=8.8 Hz, 1H), 4.67 (t, J=6.0 Hz, 2H), 3.68 (t, J=6.0 Hz, 2H), 1.69 (s, 4H), 1.29-1.28 (m, 12H)

ESI$^+$ m/z 459.1 (M+H)$^+$

Step 8

Synthesis of 2-(4-(3-ethynylaniline)-6-(2-methoxy-ethoxy)quinazoline-7-oxy)ethyl-4-(5,5,8,8-tetramethyl-5,6,7,8-tetralin-2-alkenylcarbamyl)benzoic acid The synthesis method is similar to step 8 in Embodiment 9.

$^1$H NMR (400 MHz, CDCl$_3$) δ 8.52 (s, 1H), 8.30 (s, 1H), 8.02 (d, J=8.4 Hz, 2H), 7.91-7.82(m, 4H), 7.59 (d, J=12.4 Hz, 2H), 7.45 (d, J=8.4 Hz, 1H), 7.32-7.21 (m, 4H), 4.69 (t, J=5.6 Hz, 2H), 4.23 (t, J=5.6 Hz, 1H), 4.15 (t, J=4.4 Hz, 2H), 3.75 (d, J=4.4 Hz, 2H), 3.36(s, 3H), 3.09(s, 1H), 1.67(s, 4H), 1.26(s, 12H); $^{13}$C NMR (125 MHz, CDCl$_3$) δ 175.9, 166.1, 164.9, 156.5, 154.5, 152.8, 148.3, 145.8, 145.7, 141.9, 139.6, 138.8, 135.0, 131.9, 130.0, 129.0, 128.8, 127.7, 127.2, 124.8, 122.7, 122.0, 118.4, 118.3, 108.9, 107.5, 103.3, 83.4, 77.5, 77.3, 77.0, 76.7, 70.3, 68.4, 66.7, 65.6, 62.7, 59.1, 35.0, 34.9, 34.4, 34.0, 31.81, 31.78, 30.6, 29.7, 21.0

ESI$^+$ m/z 713.9 (M+H)$^+$

Embodiment 17

Synthesis of 2,2'-(4-(3-ethynylaniline)quinazoline-6,7-diene)di(oxy)bis(ethyl-2,1-diene)-bis(2-(4-benzoylphenyl)propanoic acid)

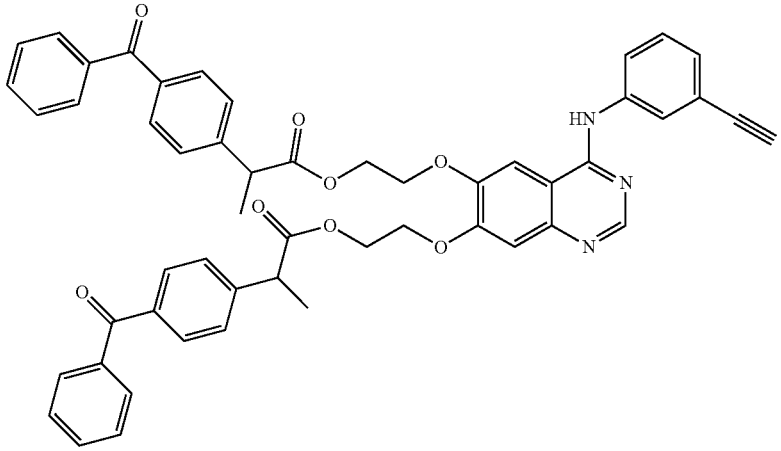 [SMILES: C#Cc1cccc(Nc2ncnc3cc(OCCOC(=O)C(C)c4ccc(C(=O)c5ccccc5)cc4)c(OCCOC(=O)C(C)c4ccc(C(=O)c5ccccc5)cc4)cc23)c1]

Steps 1, 2, 3, 4, 5 and 6 are similar to those in Embodiment 9.

Step 7

Synthesis of 2,2'-(4-(3-ethynylaniline)quinazoline-6,7-diene)di(oxy)bis(ethyl-2,1-diene)-bis(2-(4-benzoylphenyl)propanoic acid)

150 mg of the resulting product 6,7-dihydroxy-4-anilino-quinazoline obtained in step 5 of Embodiment 9 was added with 565 mg of the resulting product 4-(4-benzoylphenyl)-1-bromo-3-pentanone obtained in step 7 of Embodiment 9, 497 mg of anhydrous potassium carbonate, 24 mg of potassium iodide and 5 ml of dry DMF. The system was reacted overnight at 40° C. and followed by TLC until the reaction finished. The reaction solution was diluted with water, extracted with ethyl acetate, washed with saturated sodium chloride solution, dried with anhydrous sodium sulfate and concentrated in vacuum. The crude product was separated by column chromatography to obtain 320 mg of the resulting product 2,2'-(4-(3-ethynylaniline)quinazoline-6,7-diene)di(oxy)bis(ethyl-2,1-diene)-bis(2-(4-benzoylphenyl)propanoic acid) (71%).

$^1$H NMR (400 MHz, CDCl$_3$) δ 8.64 (s, 1 H), 8.27 (br., 1 H), 7.94 (s, 1 H), 7.83-7.14 (m, 23 H), 4.52 (t, J=4.4 Hz, 2 H), 4.47-4.37 (m, 2 H), 4.24-4.18 (m, 4 H), 3.90-3.80 (m, 2 H), 3.06 (s, 1 H), 1.58 (d, J=7.2 Hz, 3 H), 1.55 (dd, J=3.2, 6.8 Hz, 3 H); $^{13}$C NMR (125 MHz, CDCl$_3$) δ 186.0, 187.0, 174.4, 173.7, 156.4, 153.8, 147.8, 140.6, 140.5, 139.0, 137.8, 137.7, 137.2, 137.0, 132.5, 132.4, 131.5, 131.4, 129.8, 129.2, 128.93, 128.92, 128.90, 128.86, 128.74, 128.70, 128.5, 128.4, 128.3, 128.19, 128.16, 128.12, 128.09, 127.3, 124.9, 121.5, 122.0, 109.5, 109.0, 103.8, 83.4, 77.3, 77.2, 77.0, 76.7, 66.65, 66.60, 62.5, 62.0, 45.2, 45.1, 18.4, 18.3

ESI$^+$ m/z 838.2 (M+H)$^+$

Embodiment 18

Synthesis of 2,2'-(4-(3-ethynylaniline)quinazoline-6,7-diene)di(oxy)bis(ethyl-2,1-diene)-bis(2-(4-isobutylphenyl)propanoic acid)

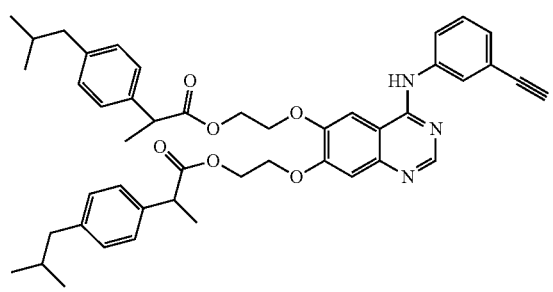 [SMILES: C#Cc1cccc(Nc2ncnc3cc(OCCOC(=O)C(C)c4ccc(CC(C)C)cc4)c(OCCOC(=O)C(C)c4ccc(CC(C)C)cc4)cc23)c1]

The synthesis method is similar to Embodiment 17.

$^1$H NMR (400 MHz, CDCl$_3$) δ 8.65 (s, 1 H), 8.29 (br., 1 H), 7.99 (s, 1 H), 7.93 (d, J=8.0 Hz, 1 H), 7.63 (s, 1 H), 7.31-7.03 (m, 11 H), 4.52-4.41 (m, 4 H), 4.20-4.18 (m, 4 H), 3.78-3.73 (m, 2 H), 3.09 (s, 1 H), 2.41 (d, J=7.2 Hz, 4 H), 1.83-1.78 (m, 2 H), 1.55 (d, J=6.4 Hz, 3 H), 1.50 (d, J=7.2 Hz, 3 H), 0.88 (d, J=6.8 Hz, 12 H); $^{13}$C NMR (125 MHz, CDCl$_3$) δ 175.3, 174.4, 156.2, 153.6, 153.4, 147.7, 146.9, 140.5, 140.3, 139.0, 137.2, 137.0, 129.2, 129.1, 128.6, 127.1, 126.9, 124.5, 122.4, 121.7, 109.2, 108.6, 103.2, 83.3, 77.3, 77.25, 77.0, 76.7, 66.5, 66.3, 62.2, 61.5, 44.8, 44.74, 44.71, 29.9, 22.13, 22.11, 18.4, 18.3

Embodiment 19

Synthesis of 2,2'-(4-(3-ethynylaniline)quinazoline-6,7-diene)di(oxy)bis(ethyl-2,1-diene)-bis(2-acetoxylbenzoic acid)

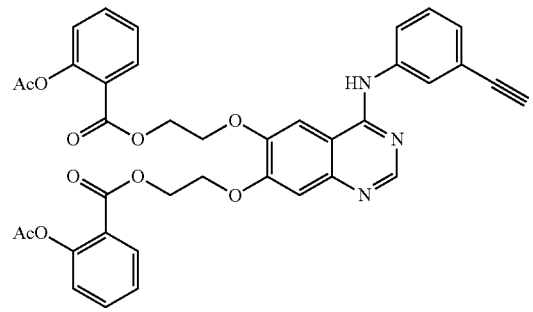 [SMILES: C#Cc1cccc(Nc2ncnc3cc(OCCOC(=O)c4ccccc4OC(C)=O)c(OCCOC(=O)c4ccccc4OC(C)=O)cc23)c1]

Steps 1, 2, 3, 4, 5 and 6 are similar to those in Embodiment 9.

Synthesis of 2,2'-(4-(3-ethynylaniline)quinazoline-6,7-diene)di(oxy) diethanol

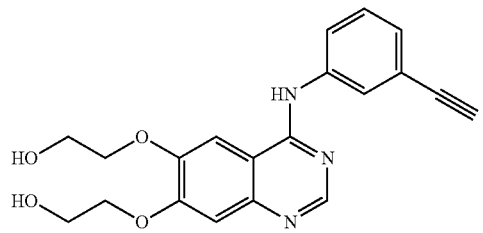 [SMILES: C#Cc1cccc(Nc2ncnc3cc(OCCO)c(OCCO)cc23)c1]

500 mg of the resulting product 6,7-dihydroxy-4-anilino-quinazoline obtained in step 5 of Embodiment 9 was added with 903 mg of 2-bromoethyl acetate, 1.24 g of anhydrous potassium carbonate, 150 mg of potassium iodide and 10 ml of dry DMF. The system was reacted overnight at 50° C. and followed by TLC until the reaction finished. The reaction solution was diluted with water, extracted with ethyl acetate, washed with saturated sodium chloride solution, dried with anhydrous sodium sulfate and concentrated in vacuum. The crude product was directly put into the next step of reaction without separation.

The crude product was dissolved in 20 ml of methanol and then added with 500 mg of KOH. The system was reacted overnight at room temperature and followed by TLC until the reaction finished. The reaction solution was directly concentrated in vacuum and separated by column chromatography to obtain 520 mg of the resulting product 2,2'-(4-(3-ethynylaniline)quinazoline-6,7-diene) di(oxy)diethanol (79%).

ESI$^+$ m/z 366.0 (M+H)$^+$

Step 8

Synthesis of 2,2'-(4-(3-ethynylaniline)quinazoline-6,7-diene)di(oxy) bis(ethyl-2,1-diene)-bis(2-acetoxyl benzoic acid)

260 mg of the resulting product 2,2'-(4-(3-ethynylaniline)quinazoline-6,7-diene)di(oxy)diethanol obtained in step 7 was dissolved in 1 ml of dry THF, and then the mixture was added with 0.65 ml of dry Et₃N in an ice bath, stirred for 10 min and slowly added with a solution of 430 mg of o-acetyl-benzoyl chloride dissolved in 3 ml of dry THF. The system was allowed to naturally rise up to room temperature, reacted and followed by TLC until the reaction finished. The reaction solution was diluted with water, extracted with ethyl acetate, washed with saturated sodium chloride solution, dried with anhydrous sodium sulfate and concentrated in vacuum. The crude product was separated by column chromatography to obtain 270 mg of the resulting product 2,2'-(4-(3-ethynylaniline)quinazoline-6,7-diene)di(oxy)bis(ethyl-2,1-diene)-bis(2-acetoxyl benzoic acid) (54%).

¹H NMR (400 MHz, CDCl₃) δ 8.58 (s, 1 H), 8.39 (br., 1 H), 7.91-6.95 (m, 14 H), 4.56-4.67 (m, 4 H), 4.24-4.17 (m, 4 H), 3.11 (s, 1 H), 2.27 (s, 6 H); ¹³C NMR (125 MHz, CDCl₃) δ 169.42, 169.39, 164.1, 163.8, 156.2, 153.8, 153.3, 150.4, 150.3, 150.1, 147.9, 146.8, 138.7, 135.6, 133.9, 133.8, 131.43, 131.36, 129.7, 129.6, 128.4, 127.2, 125.8, 124.8, 123.5, 123.3, 122.3, 122.1, 118.9, 111.7, 109.2, 108.3, 83.2, 77.35, 77.26, 77.0, 76.7, 67.4, 66.4, 62.9, 62.6, 20.7, 20.6

Embodiment 20

Synthesis of 3,3'-(4-(3-ethynylaniline)quinazoline-6,7-diene)di(oxy)bis(ethyl-2,1-diene)-bis(propyl-3,1-diene)bis(2-(6-methoxylnaphthyl-2-ene)propanoic acid)

Embodiment 21

Synthesis of 2,2'-(4-(3-ethynylaniline)quinazoline-6,7-diene)di(oxy)bis(ethyl-2,1-diene)-bis(7-7-tert-butyl-6-chloro-2-(trifluoromethyl)-2H-pyran-3-carboxylic acid)

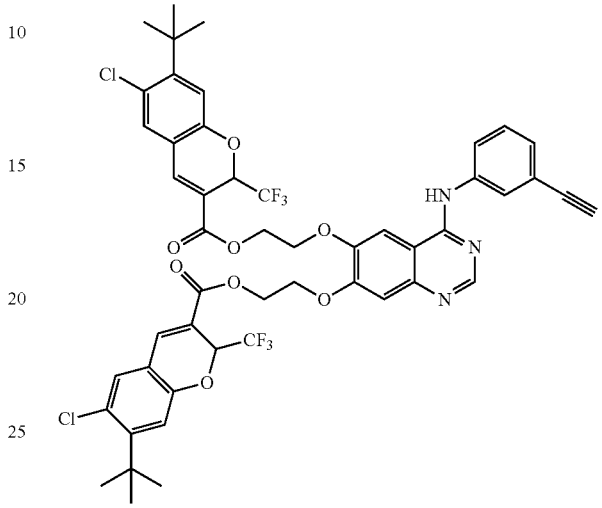

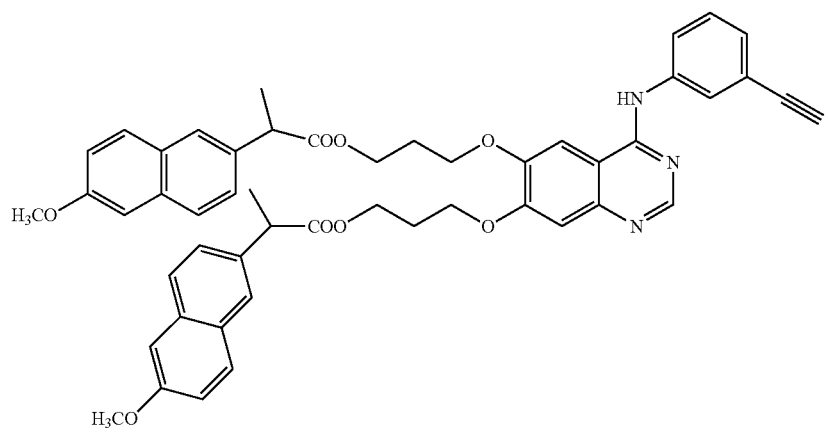

The synthesis method is similar to Embodiment 17.

¹H NMR (400 MHz, CDCl₃) δ 8.69 (s, 1 H), 8.05-6.98 (m, 19 H), 4.50 (m, 2 H), 4.36 (t, J=6.0 Hz, 2 H), 4.22 (m, 2 H), 4.08 (t, J=6.0 Hz, 2 H), 3.94-3.69 (m, 8 H), 3.13 (s, 1 H), 1.66 (d, J=6.8 Hz, 3 H), 1.57 (d, J=7.2 Hz, 3 H); ¹³C NMR (125 MHz, CDCl₃) δ 175.5, 174.4, 157.7, 157.5, 156.1, 153.7, 153.6, 147.6, 147.1, 139.1, 135.3, 135.0, 133.7, 133.5, 129.08, 129.07, 128.84, 128.78, 128.7, 127.2, 127.0, 126.0, 125.9, 125.7, 124.3, 122.6, 121.5, 119.1, 118.7, 109.2, 108.8, 105.5, 105.4, 102.9, 83.5, 77.33, 77.25, 77.0, 76.7, 66.5, 66.1, 62.4, 61.3, 55.2, 55.1, 45.34, 45.32, 45.2, 18.44, 18.40

The synthesis method is similar to Embodiment 17.

¹H NMR (400 MHz, MeOD) δ 8.38 (s, 1 H), 7.94 (s, 1 H), 7.83 (s, 1 H), 7.75 (d, J=8.0 Hz, 1 H), 7.62 (d, J=2.0 Hz, 1 H), 7.53 (d, J=4.0 Hz, 1 H), 7.36 (t, J=8.0 Hz, 1 H), 7.25-7.23 (m, 2 H), 7.17 (s, 1 H), 7.06 (s, 1 H), 6.98 (s, 1 H), 5.73 (dt, J=6.8, 12.0, 18.8 Hz, 1 H), 4.77-4.74 (m, 2 H), 4.65-4.61 (m, 2 H), 4.53-4.52 (m, 2 H), 3.51 (s, 1 H), 1.44 (s, 9 H), 1.41 (s, 9 H); ¹³C NMR (125 MHz, CDCl₃) δ 164.2, 163.4, 156.3, 154.0, 152.8, 152.4, 151.6, 151.6, 148.0, 147.5, 138.9, 137.1, 136.4, 131.9, 131.8, 129.0, 127.6, 127.0, 126.9, 124.5, 124.4, 122.7, 122.1, 121.8, 117.5, 117.3, 116.1, 115.8, 115.6, 115.5, 109.5, 109.4, 103.3, 83.4, 77.3, 77.0, 76.7, 71.1, 70.8, 70.6, 70.3, 66.7, 66.5, 63.2, 62.3, 36.6, 29.2

Embodiment 22

Synthesis of 2,2'-(4-(3-ethynylaniline)quinazoline-6,7-diene)di(oxy)bis(ethyl-2,1-diene)-bis(2-(1-(4-chlorobenzoyl)-5-methoxy-2-methyl-1H-indol-3-ene)acetic acid)

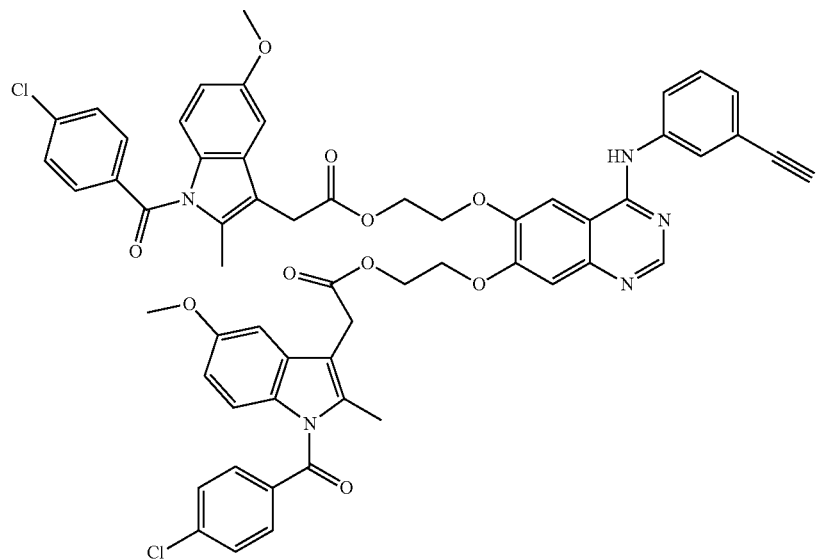 [SMILES: C#Cc1cccc(Nc2ncnc3cc(OCCOC(=O)Cc4c(C)n(C(=O)c5ccc(Cl)cc5)c5ccc(OC)cc45)c(OCCOC(=O)Cc4c(C)n(C(=O)c5ccc(Cl)cc5)c5ccc(OC)cc45)cc23)c1]

The synthesis method is similar to Embodiment 17.

Embodiment 23

Synthesis of (E)-2,2'-(4-(3-ethynylaniline)quinazoline-6,7-diene)di(oxy)bis(ethyl-2,1-diene)-bis(2-((E)-5-fluoro-2-methyl-1-(4-methylsulfinyl)benzylidene)-1H-indene-3-ene)acetic acid)

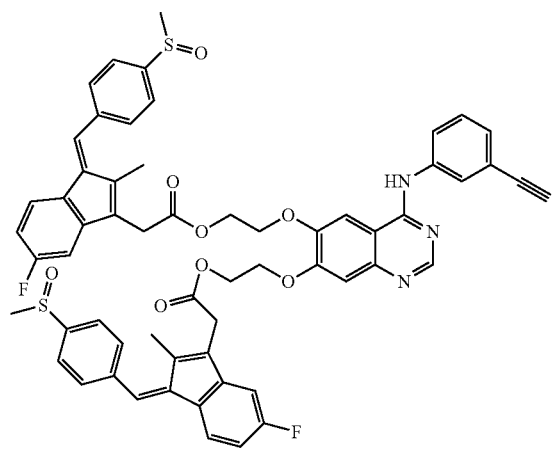 [SMILES: C#Cc1cccc(Nc2ncnc3cc(OCCOC(=O)CC4=C(C)/C(=C\c5ccc(S(C)=O)cc5)c5ccc(F)cc54)c(OCCOC(=O)CC4=C(C)/C(=C\c5ccc(S(C)=O)cc5)c5ccc(F)cc54)cc23)c1]

Steps 1, 2, 3, 4, 5, 6 and 7 are similar to those in Embodiment 19.

Step 8

Synthesis of (E)-2,2'-(4-(3-ethynylaniline)quinazoline-6,7-diene)di(oxy)bis(ethyl-2,1-diene)-bis(2-((E)-5-fluoro-2-methyl-1-(4-methylsulfinyl)benzylidene)-1H-indene-3-ene)acetic acid)

741 mg of sulindac was dissolved in 5 ml of dry THF, and the mixture was added with 430 mg of DCC in an ice bath and then stirred. The system was reacted for 2 hrs at 0° C. to obtain an active ester for standby.

185 mg of the resulting product 2,2'-(4-(3-ethynylaniline)quinazoline-6,7-diene)di(oxy)diethanol obtained in step 7 of Embodiment 19 was dissolved in 6 ml of dry THF, and then the mixture was added with 30 mg of DMAP and then slowly added with the active ester in an ice bath. The system was allowed to naturally rise up to room temperature, reacted overnight and followed by TLC until the reaction finished. The reaction solution was diluted with water, extracted with ethyl acetate, washed with saturated sodium chloride solution, dried with anhydrous sodium sulfate and concentrated in vacuum. The crude product was separated by column chromatography to obtain 250 mg of the resulting product (E)-2,2'-(4-(3-ethynylaniline)quinazoline-6,7-diene)di(oxy) bis(ethyl-2,1-diene)-bis(2-((E)-5-fluoro-2-methyl-1-(4-methylsulfinyl)benzylidene)-1H-indene-3-ene) acetic acid) (46%).

$^1$H NMR (400 MHz, CDCl$_3$) δ 8.64 (d, J=4.0 Hz, 1 H), 7.68-7.08 (m, 18 H), 6.86-6.83 (m, 2 H), 6.50 (t, J=8.8 Hz, 2 H), 4.55-4.49 (m, 4 H), 4.31-4.30 (m, 4 H), 3.61-3.59(m, 4 H), 3.08 (s, 1 H), 2.79-2.77 (m, 6 H), 2.15-2.14 (m, 6 H); $^{13}$C NMR (125 MHz, CDCl$_3$) δ170.7, 170.0, 164.1, 162.20, 162.16, 156.4, 153.8, 153.7, 148.0, 147.4, 146.6, 146.5, 146.4, 145.3, 145.2, 141.4, 141.3, 139.6, 139.4, 139.0, 138.5, 138.4, 131.41, 131.4, 129.39, 129.37, 128.8, 128.5, 128.2, 127.4, 124.9, 123.78, 123.77, 123.63, 123.55, 123.5, 122.5, 122.1, 110.8, 110.7, 110.65, 110.55, 109.4, 109.0, 106.1, 106.0, 105.8, 103.4, 83.5, 77.3, 77.0, 76.7, 66.9, 66.6, 62.7, 43.71, 43.66, 31.6, 31.5, 10.4

ESI$^+$ m/z 1042.7 (M+H)$^+$

Embodiment 24

Synthesis of 2,2'-(4-(3-ethynylaniline)quinazoline-6,7-diene)di(oxy)bis(ethyl-2,1-diene)-bis(4-(5,5,8,8-tetramethyl-5,6,7,8-tetralin-2-alkenylcarbamyl)benzoic acid)

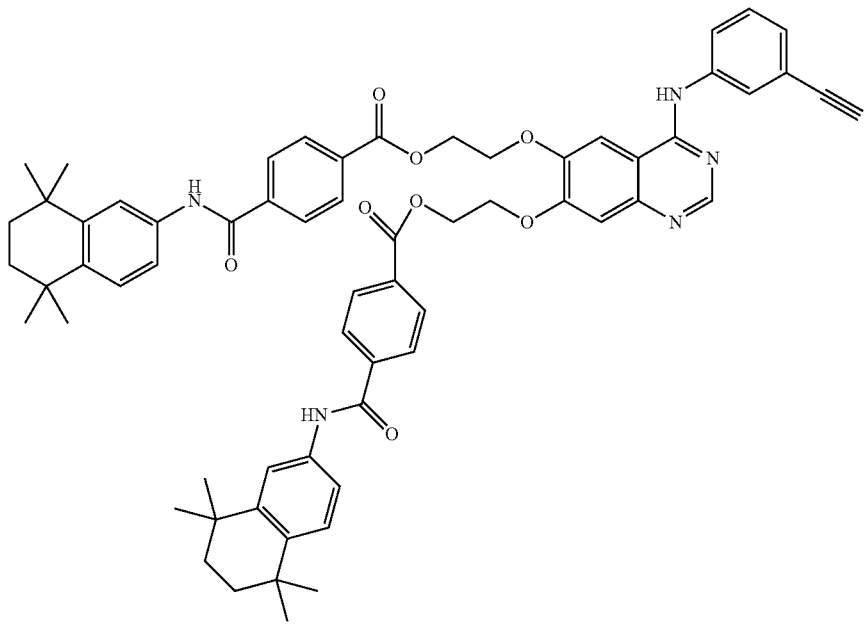 [SMILES: C#Cc1cccc(Nc2ncnc3cc(OCCOC(=O)c4ccc(C(=O)Nc5ccc6c(c5)C(C)(C)CCC6(C)C)cc4)c(OCCOC(=O)c4ccc(C(=O)Nc5ccc6c(c5)C(C)(C)CCC6(C)C)cc4)cc23)c1]

The synthesis method is similar to Embodiment 17.

$^1$H NMR (400 MHz, CDCl$_3$) δ 8.69-8.56 (m, 3 H), 7.93-7.21 (m, 19 H), 4.69 (s, 2 H), 4.54 (s, 2 H), 4.39 (s, 2 H), 4.31 (s, 2 H), 3.05 (s, 1 H), 1.66-1.65 (m, 8 H), 1.28-1.24 (m, 24 H); $^{13}$C NMR (125 MHz, CDCl$_3$) δ 165.7, 165.5, 156.6, 153.84, 153.78, 148.2, 147.2, 145.8, 145.7, 141.8, 139.6, 139.3, 138.9, 135.2, 135.1, 132.1, 131.7, 129.9, 129.8, 129.7, 128.9, 127.6, 127.25, 127.16, 127.1, 125.1, 122.6, 122.3, 118.41, 118.37, 109.6, 108.9, 103.4, 83.4, 77.3, 77.0, 76.7, 66.9, 66.7, 63.0, 62.8, 38.7, 34.98, 34.96, 34.3, 34.0, 31.8, 31.74, 31.72

ESI$^+$ m/z 1033.2 (M+H)$^+$

The following shows the results of bioactivity assay of the compounds provided by the present invention.

Material for Experiments

H1975/HCC827: human non-small cell lung cancer cells, PBS, MTT, DMEM culture medium, pancreatin, a multichannel pipette, a vortex mixer, a microplate reader, a biosafety cabinet, a 5% CO$_2$ cell culture incubator, a cell counter, a microscope, a thermostatic water bath, and a 96-pore plate.

Methods:

1. H1975/HCC827 cells was cleaned with PBS, digested with pancreatin, centrifuged at room temperature for 5 min at 1000 rpm, re-suspended with an appropriate amount of culture medium, and counted by a cell counting plate. The cells were inoculated to the 96-pore plate by the multichannel pipette at 1000-2000 cells/pore/100 μl, with 6 complex pores for each concentration and totally 6 concentration gradients. The basis of the number of cells: upon final test, OD570 was between 0.2-0.8 (Lambert-Beer's Law).

2. The compounds were prepared into 10 mol/l of mother liquor by using DMSO. 10 μl of mother liquor was added into 90 μl of DMSO, and the mixture was uniformly mixed by the vortex mixer and diluted in turn for 5 times to obtain DMSO stock solution. The stock solution was stored at 4° C. for standby. The stock solution was uniformly mixed again before use and then added into a complete culture medium in 1:500 to serve as working solution, and then the mixture was mixed uniformly by the vortex mixer. The working solution needs to be immediately used after prepared well to avoid precipitation after long-term storage.

3. The 96-pore plate was cultured in the cell incubator for 24 hrs, then added with 100 μl of the working solution prepared from the compounds, and continued to be cultured together for 72 hrs.

4. The upper-layer culture medium was removed carefully, then 100 μl of culture medium containing MTT (0.5 mg/ml) was added again, and the culture medium was placed in the incubator for 4 hrs. The culture medium was removed completely, then 100 μl of DMSO was added, and the mixture was shocked uniformly. Preparation of MTT: 1.25 g of MTT was added into 250 ml of PBS, and then the mixture was mixed uniformly and stored away from light at 4° C.

5. The light absorption value at 570 nm or 490 nm was detected by the microplate reader. EC50 was calculated and an added value curve was drawn by Graphpad.

The following table shows data of bioactivity of some of compounds.

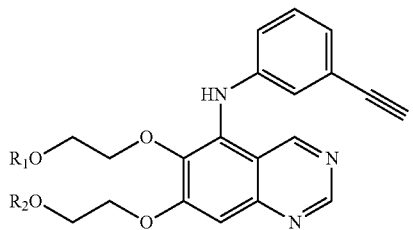
| Compound No. | Structure of compound | Cell activity ($EC_{50}$) | |
|---|---|---|---|
| | | HCC827 | H1975 |
| Embodiment 1 | $R_2$ = Me, $R_1$ = | NA | NA |
| Embodiment 2 | $R_2$ = Me, $R_1$ = | NA | NA |
| Embodiment 3 | $R_2$ = Me, $R_1$ = | 0.16 | 12.24 |
| Embodiment 4 | $R_2$ = Me, $R_1$ = | 0.61 | 32.92 |
| Embodiment 5 | $R_2$ = Me, $R_1$ = | NA | NA |
| Embodiment 6 | $R_2$ = Me, $R_1$ = | NA | NA |

-continued
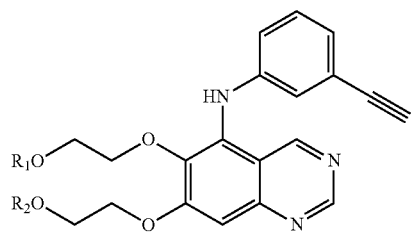
| Compound No. | Structure of compound | Cell activity (EC$_{50}$) | |
|---|---|---|---|
| | | HCC827 | H1975 |
| Embodiment 7 | 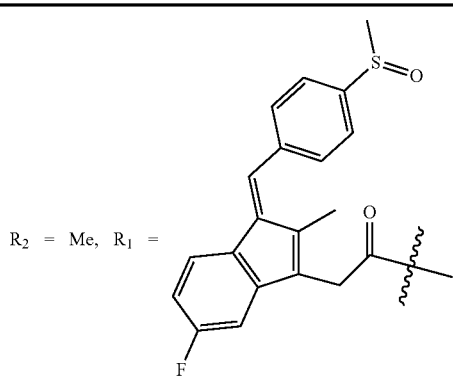 | NA | NA |
| Embodiment 8 | 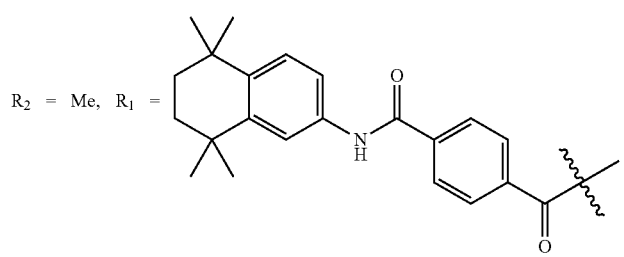 | NA | NA |
| Embodiment 9 | 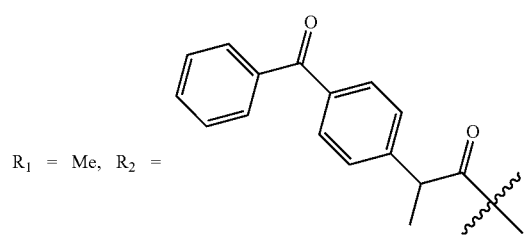 | NA | NA |
| Embodiment 10 | 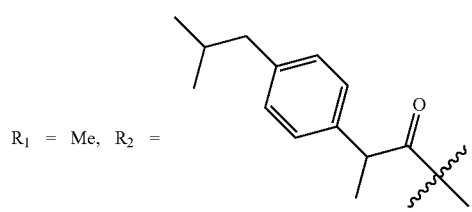 | 0.28 | 8.65 |
| Embodiment 11 | 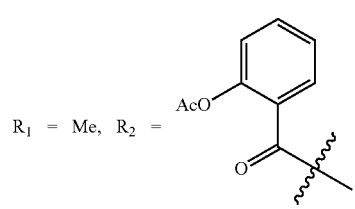 | 0.13 | 13.8 |

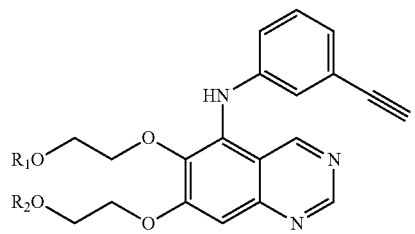
| Compound No. | Structure of compound | Cell activity (EC$_{50}$) | |
|---|---|---|---|
| | | HCC827 | H1975 |
| Embodiment 12 | R$_1$ = Me, R$_2$ = 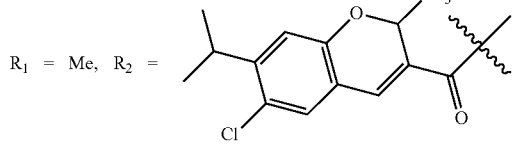 | NA | NA |
| Embodiment 13 | R$_1$ = Me, R$_2$ = 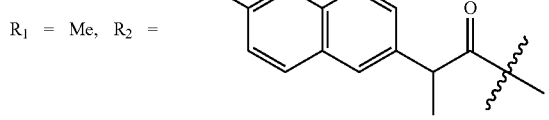 | 0.09 | 27.2 |
| Embodiment 14 | R$_1$ = Me, R$_2$ = 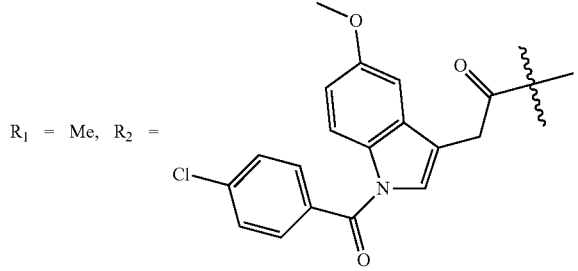 | 0.63 | 95.81 |
| Embodiment 15 | R$_1$ = Me, R$_2$ = 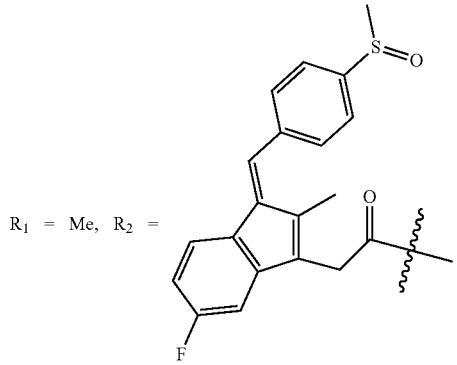 | NA | NA |
| Embodiment 16 | R$_1$ = Me, R$_2$ = 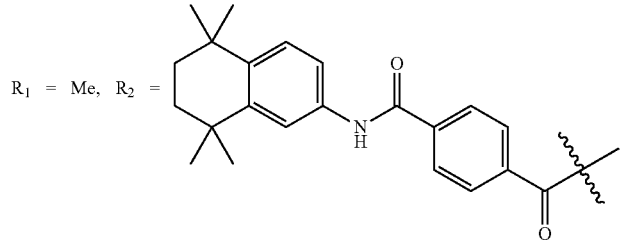 | NA | NA |

-continued
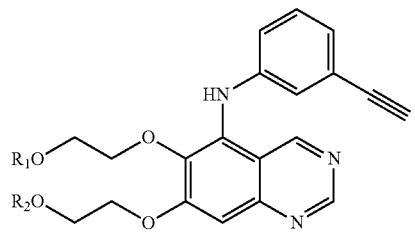
| Compound No. | Structure of compound | Cell activity (EC$_{50}$) | |
|---|---|---|---|
| | | HCC827 | H1975 |
| Embodiment 17 | R$_1$ = R$_2$ = (structure) | 1.50 | NA |
| Embodiment 18 | R$_1$ = R$_2$ = (structure) | NA | 805 |
| Embodiment 19 | R$_1$ = R$_2$ = (structure) | 0.20 | 41.66 |
| Embodiment 20 | R$_1$ = R$_2$ = (structure) | NA | NA |
| Embodiment 21 | R$_1$ = R$_2$ = (structure) | 1.05 | 75.62 |
| Embodiment 22 | R$_1$ = R$_2$ = (structure) | 3.62 | 55.31 |

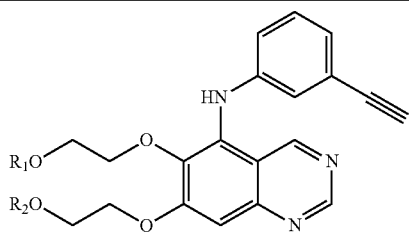

| Compound No. | Structure of compound | Cell activity (EC$_{50}$) | |
|---|---|---|---|
| | | HCC827 | H1975 |
| Embodiment 23 | R$_1$ = R$_2$ = | NA | NA |
| Embodiment 24 | R$_1$ = R$_2$ = | 1.14 | 52.94 |

The embodiments mentioned above are merely several implementations of the present invention. Although these embodiments have been described specifically and in details, these embodiments shall not be regarded as any limitation to the patent scope of the present invention. It should be pointed out that, those skilled in the art may make various variations and improvements without departing from the concept of the present invention, and those variations and improvements shall fall into the protection scope of the present invention. Therefore, the protection scope of the present invention is subject to the claims.

The invention claimed is:

1. A coupling compound selected from the group consisting of:
  2-(4-(3-ethynylanitine)-7-(2-methoxyethoxy)quinazoline-6-oxy)ethyl-2-(4-benzoylbenzene)propanoic acid,
  2-(4-(3-ethynylaniline)-7-(2-methoxyethoxy)quinazoline-6-oxy)ethyl-2-(4-isobutylbenzene)propanoic acid,
  2-(4-(3-ethynylaniline)- 7-(2-methoxyethoxy) quinazoline-6-oxy)ethyl-2-acetoxybenzoic acid,
  2-(4-(3-ethynylaniline)-7-(2-methoxyethoxy)quinazoline-6-oxy)ethyl-2-(6-methoxylnaphthyl-2-ene)propanoic acid,
  2-(4-(3-ethynylaniline)-7-(2-methoxyethoxy)quinazoline-6-oxy)ethyl-7-tert-butyl-6-chloro-2-(trifluoromethyl)-2H-pyran-3-carboxylic acid,
  3-(4-(3-ethynylaniline)-7-(2-methoxyethoxy)quinazoline-6-oxy)ethyl-2-(1-(4-chlorobenzoyl)-5-methoxy-2-methyl-1H-indol-3-ene)acetic acid,
  (E)-2-(4-(3-ethynylaniline)-7-(2-methoxyethoxy)quinazoline-6-oxy)ethyl-2-(5-fluoro-2-methyl-1-(4-methylsulfinyl)benzylidene)-1H-indene-3-ene)acetic acid,
  2-(4-(3-ethynylaniline)-7-(2-methoxyethoxy)quinazoline-6-oxy)ethyl-4-(5,5,8,8-tetramethyl-5,6,7,8-tetralin-2-alkenylcarbamyl)benzoic acid,
  2-(4-(3-ethynylaniline)-6-(2-methoxyethoxy)quinazoline-7-oxy)ethyl-2-(benzoylpheny)propanoic acid,
  2-(4-(3-ethynylaniline)-6-(2-methoxyethoxy)quinazoline-7-oxy)ethyl-2-(4-isobutylphenyl)propanoic acid,
  2-(4-(3-ethynylaniline)-6-(2-methoxyethoxy)quinazoline-7-oxy)ethyl-2-acetoxyl benzoic acid,
  2-(4-(3-ethynylaniline)-6-(2-methoxyetboxy)quinazoline-7-oxy)ethyl-2-(6-methoxylnaphthyl-2-ene)propanoic acid,
  2-(4-(3-ethynylaniline)-6-(2-methoxyethoxy)quinazoline-7-oxy)ethyl-7-tert-butyl-6-chloro-2-(trifluoromethyl)-2H-pyran-3-carboxylic acid,
  3-(4-(3-ethynylaniline)-6-(2-methoxyethoxy)quinazoline-7-oxy)ethyl-2-(1-(4-chlorobenzoyl)-5-methoxy-2-methyl-1H-indol-3-ene)acetic acid,
  (E)-2-(4-(3-ethynylaniline)-6-(2-methoxyethoxy)quinazoline-7-oxy)ethyl-2-(5-fluoro-2-methyl-1-(4-methylsulfinyl)benzylidene)-1H-indene-3-ene)acetic acid, 2-(4-(3-ethynylaniline)-6-(2-methoxyethoxy)quinazoline-7-oxy)ethyl-4-(5,5,8,8-tetramethyl-5,6,7,8-tetralin-2-alkenylcarbamyl)benzoic acid, 2,2'-(4-(3-ethynylaniline)quinazoline-6,7-diene)di(oxy)bis(ethyl-2,1-diene)-bis(2-(4-benzoylphenyl)propanoic acid), 2,2'-(4-(3-ethynylaniline)quinazoline-6,7-diene)di(oxy)bis(ethyl-2,1-diene)-bis(2-(4-isobutylphenyl)propanoic acid), 2,2'-(4-(3-ethynylaniline)quinazoline-6,7-diene)di(oxy)bis(ethyl-2,1-diene)-bis(2-acetoxyl benzoic acid), 3,3'-(4(3-ethynylaniline)quinazoline-6,7-diene)di(oxy)bis(ethyl-2,1-diene)-bis(propyl-3,1-diene)bis(2-(6-methoxylnaphthyl-2-ene)propanoic acid), 2,2'-(4-(3-ethynylaniline)quinazoline-6,7-diene)di(oxy)bis(ethyl-2,1-diene)-bis(7-7-tert-butyl-6-chloro-2-(trifluoromethyl)-2H-pyran-3-carboxylic acid), 2,2'-(4-(3-ethynylaniline)quinazoline-6,7-diene)di(oxy)bis(ethyl-2,1-diene)-bis(2-(1-(4-chlorobenzoyl)-5-methoxy-2-methyl- 1H-indol-3-ene)acetic acid), (E)-2,2'-(4-(3-ethynylaniline)quinazoline-6,7-diene)di(oxy)bis(ethyl-2,1-diene)-bis(2-((E)-5-fluoro-2-methyl-1-(4-methylsulfinyl)benzylidene)-1H-indene-3-ene)acetic acid), and 2,2'(4-(3-ethynylaniline)quinazoline-6,7-diene)di(oxy)bis(ethyl-2,1-diene)-bis(4-(5,5,8,8-tetramethyl-5,6,7,8-tetralin-2-alkenylcarbamyl)benzoic acid).

2. The compound of claim 1, selected from the group consisting of:

2-(4-(3-ethynyliline)-7-(2-methoxyethoxy)quinazoline-6-oxy)ethyl-2-acetoxybenzoic acid, 2-(4-(3-ethynylaniline)-7-(2-medioxyethoxy)quinazoline-6-oxy)ethyl-2-(6-methoxylnaphthyl-2-ene)propanoic acid, 2-(4-(3-ethynylaniline)-6-(2-methoxyethoxy)quinazoline-7-oxy)ethyl-2-(4-isobutylphenyl)propanoic acid, 2-(4-(3-ethynylaniline)-6-(2-methoxyethoxy)quinazoline-7-oxy)ethyl-2-acetoxyl benzoic acid, 2-(4-(3-ethynylaniline)-6-(2-methoxyethoxy)quinazoline-7-oxy)ethyl-2-(6-methoxylnaphthyl-2-ene)propanoic acid, 3-(4(3-ethynylaniline)-6-(2-methoxyethoxy)quinazoline-7-oxy)ethyl -2-(1-(4-chlorobenzoyl)-5-methoxy-2-methyl-1H-indol -3-ene)acetic acid, 2,2'-(4-(3-ethynylaniline)quinazoline-6,7-diene)di(oxy)bis(ethyl-2,1-diene)-bis(2-(4-benzoylphenyl)propanoic acid), 3,3'-(4-(3-ethynylaniline)quinazoline-6,7-diene)di(oxy)bis(ethyl-2,1-dien)-bis(propyl-3,1-diene)bis(2-(6-methoxylnaphthyl-2-ene)propanoic acid), 2,2'-(4,-(3-ethynylaniline)quinazoline-6,7-diene)di(oxy)bis(ethyl-2,1-diene)-bis(7-7-tert-butyl-6-chloro-2-(trifluoromethyl-2H-pyran-3-carboxylic acid), and 2,2'-(4-(3-ethynylaniline)quinazoline-6,7-diene)di(oxy)bis(ethyl-2,1-diene)-bis(4-(5,5,8,8-tetramethyl-5,6,7,8-tetralin-2-alkenylcarbamyl)benzoic acid).

3. The pharmaceutically acceptable salts or stereoisomers of the coupling compound of claim 1.

* * * * *